(12) United States Patent
Imai et al.

(10) Patent No.: US 8,481,497 B2
(45) Date of Patent: Jul. 9, 2013

(54) THERAPEUTIC AGENT FOR CANCER, AND METHOD FOR TREATMENT OF CANCER

(75) Inventors: Kohzoh Imai, Hokkaido (JP); Shigeru Sasaki, Hokkaido (JP); Tsutomu Seito, Gunma (JP)

(73) Assignees: Sapporo Medical University, Hokkaido (JP); The University of Tokyo, Tokyo (JP)

( * ) Notice: Subject to any disclaimer, the term of this patent is extended or adjusted under 35 U.S.C. 154(b) by 166 days.

(21) Appl. No.: 12/601,811

(22) PCT Filed: May 29, 2008

(86) PCT No.: PCT/JP2008/001346
§ 371 (c)(1),
(2), (4) Date: Jul. 2, 2010

(87) PCT Pub. No.: WO2008/149521
PCT Pub. Date: Dec. 11, 2008

(65) Prior Publication Data
US 2011/0129524 A1    Jun. 2, 2011

(30) Foreign Application Priority Data
May 29, 2007  (JP) ................................. 2007-142308

(51) Int. Cl.
*A61K 38/00* (2006.01)
*A61K 39/395* (2006.01)
*A61K 39/44* (2006.01)
*A61K 38/21* (2006.01)
*A61P 35/00* (2006.01)

(52) U.S. Cl.
USPC ..... 514/19.3; 514/19.4; 514/19.6; 424/138.1; 424/85.4; 424/85.6; 424/85.7; 424/155.1

(58) Field of Classification Search
None
See application file for complete search history.

(56) References Cited

U.S. PATENT DOCUMENTS
6,869,789 B2 *  3/2005  Liu et al. ................. 435/232

FOREIGN PATENT DOCUMENTS
| JP | 2005-500034 | 1/2005 |
| WO | WO-02/102854 | 12/2002 |
| WO | WO/02/102854 | * 12/2002 |
| WO | WO-02/102972 | 12/2002 |
| WO | WO/2004/096224 | * 11/2004 |
| WO | WO-2005/066211 | 7/2005 |

OTHER PUBLICATIONS

Zheng et al., Synergistic anti-tumor effect of recombinant chicken fibroblast growth factor receptor-1-mediated anti-angiogenesis and low-dose gemcitabine in a mouse colon adenocarcinoma model. World J. Gastroenterol. 13, 2484-2489, 2007.*
Examination Report for European Patent Application No. 08763946, dated Jul. 22, 2011, 3 pages.
Extended European Search Report for European Patent Application No. 08763946, dated Jul. 5, 2010, 8 pages.
International Preliminary Report on Patentability for International Patent Application No. PCT/JP2008/001346, completed Jun. 16, 2009, 17 pages including English translation.
Hisaka et al., Journal of Hepatology (2004) 41(5):782-789.
Fujioka et al., Biomedical Research (2006) 27(5):219-226.
Damdinsuren et al., International Journal of Oncology (2007) 30(1):201-208.
Murata et al., Cytokine (2006) 33(3):121-128.
Damdinsuren et al., Annals of Surgical Oncology (2003) 10(10):1184-1190.
Noguchi et al., Clinical Cancer Research (2003) 9(16):6038-6045.
Torcia et al., Biochemical and Biophysical Research Communications (1999) 262(3):838-844.
Huang et al., Cancer Research (2006) 66(3):1481-1490.
Ogasawara et al., Hepatology (1996) 24:198-205.
Kin et al., Journal of Hepatology (1997) 27(4):677-687.
Karajannis et al., Leukemia (2006) 20(6):979-986.
Siffroi-Fernandez et al., Archives of Ophthalmology (2005) 123(3):368-376.
Bier et al., Cancer Immunology Immunotherapy (1998) 46(3):167-173.
Gennari et al., Clinical Cancer Research (2004) 10(17):5650-5655.
Suzuki et al., Clinical Cancer Research (2007) 13(6):1875-1882.
Liu et al., Cancer Immunology Immunotherapy (2002) 51(3):171-177.
Drinane et al., JBC Papers in Press, Published on Sep. 1, 2006 as Manuscript M607097200.
Fujita et al., International Journal of Molecular Medicine (2006) 17:605-616.

* cited by examiner

*Primary Examiner* — Elly-Gerald Stoica
(74) *Attorney, Agent, or Firm* — Morrison & Foerster LLP

(57) ABSTRACT

[PROBLEMS] To provide a technique which enables an effective antibody therapy for cancer which targets for FGFR1 without the need of using any effective antibody having high specificity and a potent cell-killing activity. [MEANS FOR SOLVING PROBLEMS] Disclosed are: a therapeutic agent for cancer, which comprises an enhancer of the expression of a fibroblast growth factor receptor-1 and an anti-fibroblast growth factor receptor-1 antibody; and a method for the treatment of cancer using the therapeutic agent.

17 Claims, 7 Drawing Sheets

0 Hour After Administration of IFN-alpha

24 Hours After Administration of IFN-alpha

| FGFR1 Up-regulation with 3 Kinds of Interferon |||| 
|---|---|---|---|
| Cell Line | IFN-alpha | IFN-beta | IFN-gamma |
| HepG2 | ++ | ++ | ++ |
| huH-7 | ++ | ++ | ++ |
| CHC4 | ++ | ++ | ++ |
| RPMI8226 | + | + | |
| HCT116 | + | + | |
| MKN-45 | + | + | |
| MKN-74 | + | + | |
| SH101 | + | + | |
| MDA-MB-435S | ++ | ++ | |
| MCF-7 | + | + | |
| MRK-nu1 | ± | ± | |
| U937 | + | + | |
| HPC-yo | + | + | |

Each assay was assessed by FACS analysis after 48hr incubation at 37°C. The concentration of interferon and ADR were 1000U/mL and 5ng/mL, respectively.

THERAPEUTIC AGENT FOR CANCER, AND METHOD FOR TREATMENT OF CANCER

REFERENCE TO SEQUENCE LISTING FILED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 643102001100Seqlist.txt | Nov. 20, 2009 | 15,562 bytes |

CROSS REFERENCE TO RELATED APPLICATIONS

This application is the national phase of PCT application PCT/JP2008/001346 which claims priority from Japanese application 2007/142308 filed 29 May 2007. The contents of these documents are incorporated herein by reference.

TECHNICAL FIELD

The present invention relates to an agent for treatment of cancer and a method for treatment of cancer, and in particular to an agent for treatment of cancer and a method for treatment of cancer combining a biologically active protein with an antibody.

BACKGROUND ART

At present, a surgery, a percutaneous therapeutic method of utilizing ultrasound or electromagnetic waves, and a transcatheter therapeutic method are employed as a method for treatment of cancer. These methods can selectively remove and kill cancer cells to make the methods useful for topical control, and are expected to exert further topical control capability.

However, nevertheless their topical control capability, these methods are not sufficient to improve prognosis at the current situation. One possible reason is that repeated treatment with these methods influences normal cells around cancer cells, and thereby causes deterioration in functions of organs (in the case of a liver, deterioration in hepatic preliminary performance). A primal requisite for cancer treatment in the future is to inhibit growth of cancer cells, to inhibit angiogenesis and in the case of hepatic cancer to inhibit intraportal infiltration that is a prognostic prescribed factor, and to maintain the functions of organs (hepatic preliminary performance) simultaneously.

hepatocellular carcinoma is often developed from cirrhosis hepatic C or B, and often shows a reduction in hepatic preliminary performance. Hepatic cancer readily recurs due to blood-mediated metastases (intrahepatic metastases, vascular infiltration) or development of new hepatic cancer (multicentric carcinogenesis), and is known to have a poor prognosis as a 3-year survival rate of 52.5% and a 5-year survival rate of 35.4% according to a report of 2003. These current methods for treatment of hepatic cancer are considered to have problems of such as incomplete inhibition of multicentric carcinogenesis, difficulties in control of intraportal infiltration, and impossible treatment of deterioration in hepatic functional reserve. With the aging of hepatic cancer patients, less-invasive therapies have been demanded.

Fibroblast growth factor receptor (referred to hereinafter as "FGFR") is a one-transmembrane receptor, and in mammals, there are 5 types of the receptors FGFR1 to FGFR4 and FGFR5/1L. Each of these FGFRs consists of extracellular 3 immunoglobulin (Ig)-like domains, a transmembrane domain, and intracellular 2 tyrosine kinase domains. The FGFR binds to FGF with two of the 3 Ig-like domains (Ig-like domains II and III), and thereby forms a dimer. FGFR undergoes selective splicing to produce many transcripts which gives FGFR ligand specificity.

Among these FGFRs, FGFR1 has been confirmed to be expressed in hepatic cancer and known to promote the development of hepatic cancer accompanying carcinogenic stimulation (Non-Patent Document 1). It has been reported that FGFR1 is not expressed in noncancerous hepatic cells (Non-Patent Document 2) and that FGFR1-mediated stimulation is involved not only in cell growth and cell infiltration but also in angiogenesis (Non-Patent Document 3).

From these findings, FGFR1 has been attractive target for cancer therapy. Particularly, FGFR1 has high affinity for bFGF which involved in angiogenesis, and has thus been considered as a molecular target of an anticancer agent. It has been revealed that amino acid sequence of African clawed frog (Xenopus laevis) FGFR1 has 74% and 80% homologies to that of human FGFR1 and mouse FGFR1, respectively, by Swiss plot comparative analysis and the like. A vaccine therapy with Xenopus laevis FGFR1 showed an anticancer effect, however vaccine therapy with mouse FGFR1 did not show an anticancer effect. Besides, antibodies to FGFR1 and the like have been already reported, however no effective anti-cancer drug targeting FGFR1 have been found yet.

Interferon is a cytokine known to be involved in growth inhibition of viruses and cells and in inflammatory reactions. Interferon is known to have types of type I interferon such as interferon-alpha and interferon-beta and type II interferon such as interferon-gamma. Interferon-gamma is known as a cytokine that inhibits growth and fibrillization of a human hepatic stellate cell which is known to contribute to development and progress of liver fibrosis. It is reported that, from cDNA microarray analysis, stimulation of human hepatic stellate cells with interferon-gamma reduces expression of FGFR1 (Non-Patent Document 4).

Non-Patent Document 1: Ectopic Activity of Fibroblast Growth Factor Receptor 1 in Hepatocytes Accelerates Hepatocarcinogenesis by Driving Proliferation and Vascular Endothelial Growth Factor; Induced Angiogenesis, Cancer Res 2006; 66(3): 1481-90

Non-Patent Document 2: Expressions of Basic Fibroblast Growth Factor and Its Receptors and Their Relationship to Proliferation of Human Hepatocellular Carcinoma Cell Lines, HEPATOLOGY 1996; 24: 198-205.

Non-Patent Document 3: THE ANTI-ANGIOGENIC ACTIVITY OF rPAI-123 INHIBITS FIBROBLAST GROWTH FACTOR-2 FUNCTIONS, JBC Papers in Press. Published on Sep. 1, 2006 as Manuscript M607097200

Non-Patent Document 4: Interferon-gamma down-regulates expression of tumor necrosis factor-alpha converting enzyme/a disintegrin and metalloproteinase 17 in activated hepatic stellate cells of rats, International journal of molecular medicine 17: 605-616, 2006

DISCLOSURE OF THE INVENTION

An object of the present invention is to provide a method for treatment of cancer targeting FGFR1. Particularly, the present invention is to treat cancer by using a combination of an FGFR1 expression enhancer and an anti-FGFR1 antibody against cancer cells.

The inventors made extensive study to solve the problem, and achieved the present invention by finding that stimulation with a certain biologically active protein enhances the expression of FGFR1 in cancer cells, and that an anti-FGFR1 antibody targeting FGFR1 whose expression has been enhanced by the biologically active protein can effectively inhibit growth and survival of cancer cells. Thus, the inventors found that one reason of insufficient cancer inhibitory effect of a cancer drug targeting FGFR1 is that expression of FGFR1 on cancer cells is not enough to treat cancer with the drug (for example, from the observation of histological staining, the expression of FGFR1 was very low in hepatic cancer area). Also, the inventors found that effective cancer therapy can be achieved by combining an FGFR1 expression enhancer with a molecular targeting drug that targets FGFR1, and thereby achieved the present invention. Further, the inventors obtained an anti-FGFR1 antibody that can sufficiently exhibit a therapeutic effect and has high specificity as well as a strong cell-killing action, as an active ingredient of a drug targeting FGFR1, and thereby achieved the present invention. The inventors particularly surprisingly found that, although interferon-gamma was reported to decrease the expression level of FGFR1 mRNA, interferon promotes the expression of FGFR1. Moreover, the present inventors found that certain anticancer agents etc. have an activity of enhancing the expression of FGFR1.

Specifically, the present invention relates to the following agent and method for treatment of cancer:

(1) An agent for treatment of cancer, comprising a combination of a fibroblast growth factor receptor-1 expression enhancer and an anti-fibroblast growth factor receptor-1 antibody or a fragment thereof, which are administered simultaneously, continuously, or separately at an interval.

(2) An agent for treatment of cancer, comprising a combination of a fibroblast growth factor receptor-1 expression enhancer, an anti-fibroblast growth factor receptor-1 antibody or a fragment thereof and a peripheral blood mononuclear cell, which are administered simultaneously, continuously, or separately at an interval.

(3) The agent of (1) or (2), wherein the fibroblast growth factor receptor-1 expression enhancer is interferon-alpha, interferon-beta, adriamycin, or 5-azacitidine.

(4) The agent of any one of (1) to (3), wherein an anticancer drug is bound to the anti-fibroblast growth factor receptor-1 antibody or a fragment thereof.

(5) The agent of (4), wherein the anticancer drug is a cellular toxin or a targeting liposome.

(6) The agent of any one of (1) to (5), which is an agent for treatment of hepatic cancer, gallbladder cancer, colon cancer, stomach cancer, breast cancer, pancreas cancer, myeloma, or leukemia.

(7) A method for treatment of cancer, comprising enhancing expression of fibroblast growth factor receptor-1 on cancer cells in a cancer patient and administering an anti-fibroblast growth factor receptor-1 antibody or fragment thereof.

(8) The method of (7), further comprising administrating a peripheral blood mononuclear cell.

(9) A method for treatment of cancer, comprising administering a fibroblast growth factor receptor-1 expression enhancer and an agent comprising an anti-fibroblast growth factor receptor-1 antibody or a fragment thereof to a cancer patient.

(10) The method of (9), further comprising administering an agent comprising a peripheral blood mononuclear cell.

(11) The method of (9) or (10), wherein the agents are administered simultaneously, continuously, or separately at an interval.

(12) The method of (9) or (10), wherein the fibroblast growth factor receptor-1 expression enhancer is interferon-alpha, interferon-beta, adriamycin, or 5-azacitidine.

(13) The method of (9) or (10), wherein an anticancer drug is bound to the anti-fibroblast growth factor receptor-1 antibody or a fragment thereof.

(14) The method of (13), wherein the anticancer drug is a cellular toxin or a targeting liposome.

(15) The method of (9) or (10), which is a method for treatment of hepatic cancer, gallbladder cancer, colon cancer, stomach cancer, breast cancer, pancreas cancer, myeloma, or leukemia.

(16) A method for treatment of cancer, characterized by administering interferon-alpha, interferon-beta, adriamycin, or 5-azacitidine to a cancer patient to enhance expression of fibroblast growth factor receptor-1 on hepatic cancer cells and then administering an anti-fibroblast growth factor receptor-1 antibody or a fragment thereof, thereby inhibiting growth of the hepatic cancer cells.

In the present invention, the "FGFR1 expression enhancer" is not particularly limited as long as it is a substance that enhances the expression of FGFR1 on cells. The FGFR1 expression enhancer is preferably a substance that enhances the expression of FGFR1 on cancer cells (preferably hepatic cancer cells, gallbladder cancer cells, colon cancer cells, stomach cancer cells, breast cancer cells, pancreas cancer cells, myeloma cells, or leukemia cells). The FGFR1 expression enhancer includes, for example, IFN-alpha, IFN-beta or IFN-gamma, adriamycin (hereinafter referred to as "ADR") and 5-azacitidine (hereinafter referred to as "Aza") such as decitabine and the like.

In the present invention, the "anti-FGFR1 antibody" is not particularly limited as long as it is an antibody binding to FGFR1. The anti-FGFR1 antibody of the present invention may bind to a substance other than FGFR1 without any particular limitation as long as it is applicable to cancer therapy, but preferably is the antibody which specifically binds to FGFR1. The agent or method of the present invention enhances the expression of FGFR1 on the surface of a cancer cell, thus an anticancer effect based on an ADCC activity which accompanies the binding of FGFR1 antibody to the antigen may be increased. Accordingly, the anti-FGFR1 antibody of the present invention is preferably an antibody having a strong ADCC activity. It is known that the ADCC activity of an antibody is increased by sugar chain modification (J. Biol. Chem., Vol. 278, Issue 5, 3466-3473, Jan. 31, 2003; J Immunol Methods. 2005 Nov. 30, 306 (1-2): 151-60; Clin Cancer Res. 2005 Mar. 15, 11(6): 2327-36) etc. The antibody of the present invention may have been subjected to suitable sugar chain modification in order to enhance its ADCC activity. A fragment of the antibody of the present invention may have a site to be recognized by at least an Fc receptor (Fc-gamma-RIII (CD16)) on NK cell. The antibody of the present invention or a fragment thereof may be a bi-specific antibody that recognizes both FGFR1 and Fc-gamma-RIII.

The FGFR1 recognized by the anti-FGFR1 antibody of the present invention is not particularly limited, but is preferably FGFR1 derived from mammals such as mice, rats, hamsters, rabbits and humans and is more preferably human FGFR1. The anti-FGFR1 antibody of the present invention is preferably an antibody, recognizing a polypeptide at positions 1 to 822 or positions 22 to 822 in the whole amino acid sequence (SEQ ID NO: 1) of human FGFR1.

The anti-FGFR1 antibody of the present invention may be a polyclonal or monoclonal antibody and is preferably a monoclonal antibody. The immunoglobulin class of the antibody of the present invention is not particularly limited and may be any immunoglobulin classes such as IgG, IgM, IgA, IgE, IgD and IgY. The antibody of the present invention encompasses antibodies of any isotypes.

The anti-FGFR1 antibody of the present invention encompasses a nonhuman animal antibody, an antibody having an amino acid sequence of a nonhuman animal antibody and an amino acid sequence of a human-derived antibody, and a human antibody. The nonhuman animal antibody includes, for example, those antibodies derived from mice, rats, hamsters, rabbits, chickens, ducks, etc., and is preferably an antibody of an animal from which a hybridoma can be produced, more preferably a mouse antibody. The antibody having an amino acid sequence of a nonhuman animal antibody and an amino acid sequence of a human-derived antibody includes a human chimeric antibody as well as a humanized antibody. A human chimeric antibody is an antibody in which an antigen-binding domain Fv of a human antibody is replaced with the Fv domain of an animal-derived monoclonal antibody. A humanized antibody is an antibody in which a CDR, a part of sequence on Fv domain being directly involved in binding to an antigen, of an animal-derived monoclonal antibody has been integrated into a frame region of a human antibody. The CDR as used herein is one defined by Kabat et al. ("Sequences of Proteins of Immunological Interest." Kabat, E. et al., U.S. Department of Health and Human Services, 1983) or Chothia et al. (Chothia & Lesk, J. Mol. Biol., 196, 901-917, 1987). The human antibody refers to an antibody that is completely an expression product of a human-derived antibody gene.

The present invention also encompasses a fragment of the anti-FGFR1 antibody. The "fragment of the antibody" is a part (partial fragment) of the antibody or a peptide containing a part of the antibody, which maintains the action of the antibody on its antigen. Examples of such antibody include, for example, F(ab')$_2$, Fab', Fab, single-stranded Fv (hereinafter referred to as "scFv"), disulfide bond Fv (hereinafter referred to as "dsFv") or a polymer thereof, a dimerized V region (hereinafter referred to as "diabody"), or a CDR-containing peptide.

F(ab')$_2$ is an antibody fragment with a molecular weight of about 100,000 having an antigen binding activity, among fragments obtained by treating IgG with a protease pepsin. Fab' is an antibody fragment with a molecular weight of about 50,000 having an antigen binding activity, wherein the disulfide bond in a hinge region of the F(ab') is cleaved. An scFv is a polypeptide having an antigen binding activity, wherein one VH and one VL are linked via a peptide linker. A dsFv is a fragment having an antigen binding activity, wherein amino acid residues substituted by cysteine residues in VH and VL are bound via a disulfide bond. The diabody is a scFv's dimerized fragment. The diabody of the present invention may be mono-specific or bi-specific (a multi-specific antibody). Dimerized scFv's may be the same or different. The CDR-containing peptide is a peptide containing an amino acid sequence of at least one CDR selected from CDR1, CDR2 and CDR3 in the heavy chain variable region and CDR1, CDR2 and CDR3 in the light chain variable region.

The agent or method of the present invention enhances the expression of FGFR1 on the surface of a cancer cell, and thus the anti-FGFR1 antibody or a fragment thereof may be bound to a desired anticancer drug and used for increasing the targeting capability of the anticancer drug. As used herein, the anticancer drug is not particularly limited as long as it is a drug that can exert a cancer treatment effect either directly or indirectly by activating physiological functions such as biological defense. The anticancer drug to enhance the ability to target at cancer cells by FGFR1 includes drugs known as anticancer drugs, for example an alkylating agent such as ifosfamide, cyclophosphamide, dacarbazine, temozolomide, nimustine, busulfan or melphalan; an antimetabolite such as enocitabine, capecitabine, carmofur, gemcitabine, cytarabine, tegafur, tegafur-uracil, tegafur-gimeracil-oteracil potassium (TS-1), fluorouracil, or methotrexate; a plant alkaloid such as irinotecan, etoposide, sobuzoxane, docetaxel, nogitecan, paclitaxel, vinorelbine, vincristine, vindesine, or vinblastine; an anticancer antibiotic such as actinomycin D, aclarubicin, idarubicin, epirubicin, daunorubicin, doxorubicin, pirarubicin, bleomycin, peplomycin, mitomycin C, or mitoxantrone; a platinum-containing drug such as oxaliplatin, carboplatin, cisplatin, or nedaplatin; a hormone such as anastrozole, exemestane, ethinyl estradiol, chlormadinone, goserelin, tamoxifen, bicalutamide, flutamide, prednisolone, leuprorelin, or letrozole; a biological response modifier such as interferon-alpha, interferon-beta, interferon-gamma, interleukin-2, ubenimex, dry BCG, or lentinan; molecular target drugs such as imatinib, gefitinib, gemtuzumab ozogamicin, tamibarotene, trastuzumab, tretinoin, bortezomib, or rituximab, as well as a radioisotope and a cytotoxic compound (cellular toxin) such as Zevalin, Bexxar, or Myelotarg. The anticancer drug also includes, for example, an anti-Fc-gamma-III antibody or a fragment thereof that activates complements and NK cells having an action of activating physiological functions such as biological defense (Protein Engineering Design and Selection 2008 21(1): 1-10), etc. The anti-FGFR1 antibody or a fragment thereof may be bound directly to the anticancer drug or bound to a targeting liposome containing the anticancer drug.

In the present invention, the "peripheral blood mononuclear cell" refers to a lymphocyte or monocyte separated from peripheral blood and is obtained from peripheral blood by centrifugation with a concentration gradient prepared with Ficoll™ and a cancer iodine compound metrizamide or the like. The peripheral blood mononuclear cell includes T cells, B cells, NK cells, plasma cells, activated T cells, macrophages, dendritic cells, etc. When an ADCC activity-dependent effect is particularly expected in the agent or method of the present invention, the peripheral blood mononuclear cell contains at least a certain amount of NK cells having an effect of enhancing the ADCC activity. When the peripheral blood mononuclear cell is used in expectation of the ADCC activity-dependent effect, the anti-FGFR1 antibody or a fragment thereof may have a site to be recognized by at least an Fc receptor of NK cell.

The agent or method for cancer treatment of the present invention can specifically inhibits the growth of cancer cells without influencing normal cells. Accordingly, the agent for treatment of cancer of the present invention can treat cancer without causing a reduction of functions in normal organs (hepatic preliminary performance). The cancer to which the agent or method of the present invention is applicable includes hepatic cancer, gallbladder cancer, colon cancer, stomach cancer, breast cancer, pancreas cancer, myeloma, and leukemia.

BEST MODE FOR CARRYING OUT THE INVENTION

Figure 1:
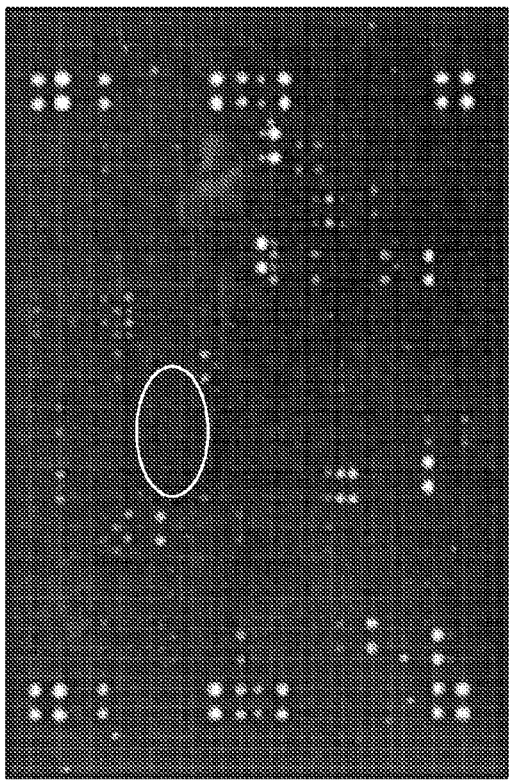
FIG. 1 shows a result of DNA array analysis in an experiment of administrating IFN-alpha using a hepatic cancer cell line HepG2-xenografted SCID mouse.
Figure 1:
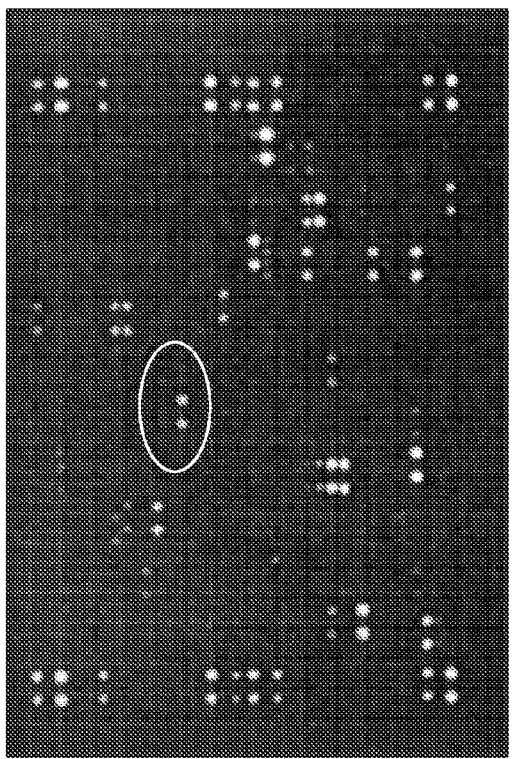

The agent for cancer treatment of the present invention (hereinafter referred to as the agent of the present invention) comprises an FGFR1 expression enhancer and an antibody against fibroblast growth factor receptor-1 or a fragment thereof as active ingredients.

The FGFR1 expression enhancer, an active ingredient of the agent of the present invention, can be obtained by determining whether a candidate substance enhances an expression of FGFR1 in cancer cells (preferably hepatic cancer cells) and then selecting the substance that enhance the expression of FGFR1. Whether a candidate substance enhances the expression of FGFR1 or not can be determined, for example, by administering the candidate substance to a cancer cell line-xenografted mouse and then measuring the mRNA or protein expression in the cancer cell line. Specifically, whether or not a candidate substance enhances the expression of FGFR1 in the cancer cells can be determined, for example, by xenografting $1\times10^5$ to $1\times10^7$ cancer cells (for example, cancer cell line HepG2 or the like) in a severe combined immunodeficient (SCID) mouse, at 2 to 4 weeks after xenografting when the size of tumor in the mouse reaches about 3 to 10 mm (preferably 5 to 8 mm) administering a candidate substance intravenously at once to several times, before and 24 hours after the administration collecting tumor tissues, and extracting mRNA from the collected tumor tissues which is then converted into cDNA to be subjected to DNA array analysis, or immunostaining the collected tumor tissues.

IFN-alpha, IFN-beta and IFN-gamma can be obtained by separation and purification from the living body or may be those distributed in the market. Commercially available IFN-alpha includes, for example, Sumiferon (Sumitomo Pharmaceuticals Co., Ltd.), OIF (Otsuka Pharmaceutical Co., Ltd.), Intron A (manufactured by Schering-Plough), Advaferon (Astellas Pharma Inc.), and Pegasis (Chugai Pharmaceutical Co., Ltd.), and Pegintron (manufactured by Schering-Plough). Commercially available IFN-beta includes, for example, Feron (Toray) and IFN-beta Mochida (Mochida Pharmaceutical Co., Ltd.).

Adriamycin and 5-azacitidine may be those distributed in the market, for example, Adriacin (registered trademark) (Kyowa Hakko Kogyo Co., Ltd.) and Vidaza (registered trademark) (Pharmion Corporation).

The anti-FGFR1 antibody can be obtained by the following method. First, a polypeptide having the whole or a part of FGFR1, or a mammal cell expression vector or the like in which a polynucleotide encoding the same was integrated, is prepared as an antigen. In preparation of a monoclonal antibody, this antigen is used to immunize an animal by a known method of preparing a monoclonal antibody, for example, a method described in "Ko-Peptido Koutai Jikken Protocol" (Anti-Peptide Antibody Experimental Protocol) authored by Shinobu Ohumi, Kunio Tsujimura, and Masaki Inagaki and published by Shujunsha, 1994, or "Tan-clone Koutai Jikken Manyuaru" (Monoclonal Antibody Experimental Manual) edited by Sakuji Toyama & Tamie Ando and published by Kodansha, 1987. Then, immunocytes obtained from the immunized animal are fused with myeloma cells to produce hybridomas, and antibodies are obtained from a culture of the hybridomas. Finally, the collected antibodies are purified by antigen-specific purification with FGFR1 used as the antigen or with a polypeptide corresponding to a part of FGFR1, whereby the FGFR1 monoclonal antibody can be obtained. Alternatively, in preparation of a polyclonal antibody, the same antigen as described above is used to immunize an animal by a known method of preparing a polyclonal antibody, for example, a method described in "Zoku Seikagaku Jikken Koza, Men-eki Seikagaku Ho" (Biochemical Experimental Lecture Series, Immunobiochemistry Research Method) (edited by Japanese Biochemical Society) or the like, and blood is collected from the immunized animal, and serum is separated from the blood and then subjected to specific antigen purification with the antigen described above, whereby the FGFR1 polyclonal antibody can be obtained.

Immunization of an animal with the antigen described above is carried out by dissolving the antigen in a sodium phosphate buffer solution (PBS) and immunizing a nonhuman mammal or bird with the resulting antigen solution, if necessary with an adjuvant (for example, mineral oil or an aluminum precipitate and heat-killed bacteria or lipopolysaccharides, or Freund's complete adjuvant or Freund's incomplete adjuvant).

FGFR1 used as the immunogen is not particularly limited as long as it is mammalian FGFR1, and preferably is human FGFR1. For example, whole amino acid sequence of human FGFR1 (SEQ ID NO: 1, Accession No. NM_023110) and its cDNA sequence (SEQ ID NO: 2, Accession No. NM_023110) have been reported. A cDNA encoding a polypeptide corresponding to the whole or a part of FGFR1 can also be obtained, through cloning, from a cDNA library of human tumor cell line or the like by using a mammal-derived FGFR1 cDNA such as FGFR1 cDNA as a probe. Accordingly, the immunogen used in preparation of the antibody of the present invention can be obtained as a recombinant protein or polypeptide by transforming *Escherichia coli*, yeasts, insect cells, animal cells or the like with an expression vector such as pGEX (for *E. coli*) or pcDNA3.1 (for animal cell expression, manufactured by Invitrogen) containing the cDNA encoding FGFR1, and then culturing the host microorganisms or cultured cells such as transformed *E. coli*, in an LB medium or the like to express the cDNA, thereby producing the intended recombinant product. When the peptide having a part of FGFR1 is used as a immunogen, the immunogen can be obtained by introducing an expression vector containing the cDNA encoding the peptide, into *Escherichia coli*, yeasts, insect cells, animal cells or the like, and then expressing the cDNA. The expressed FGFR1 or a fragment thereof can be purified with an affinity column, a nickel column, etc.

When a peptide having a part of FGFR1 is used as the immunogen, the peptide having a part of FGFR1 may be used as it is, or two or more peptides each having a part of FGFR1 may also be used as combined peptides via a linker.

FGFR1 or a peptide having a part thereof can be prepared by chemical synthesis using the Fmoc method, Boc method or the like. For example, the C-terminal amino acid of FGFR1 or of a peptide having a part thereof is immobilized on a polystyrene carrier and then reacted and bound with a 9-fluorenylmethyloxycarbonyl group (Fmoc group)- or tert-butoxycarbonyl group (Boc group)-protected amino acid by a condensation agent such as diisopropyl carbodiimide (DIC) followed washing and de-protection repeatedly, whereby a peptide having the desired amino acid sequence can be obtained.

Alternatively, FGFR1 or a peptide having a part thereof can also be synthesized with an automatic peptide synthesizer. Such peptide synthesizers include, for example, PSSM-8 (Shimadzu Corporation), a peptide synthesizer, model 433A (Applied Biosystems, Inc.), ACT396Apex (Advanced ChemTech Inc.), and the like.

The animals to be immunized are not particularly limited as long as hybridoma can be produced from the animal, and includes mice, rats, hamsters, rabbits, chickens, ducks, goats and horses and the like. The animals are preferably mice or rats, more preferably mice.

Administration of the immunogen to an animal may be carried out for example through subcutaneous injection, intraperitoneal injection, intravenous injection, subcutaneous injection, intramuscular injection or footpad injection, among which subcutaneous injection or intraperitoneal injection is preferable. The amount of the immunogen is not particularly limited as long as the antibody is produced, and is preferably 0.1 to 1000 micro g, more preferably 1 to 500 micro g, even more preferably 10 to 100 micro g. The immunization can be carried out either once or several times at suitable intervals. The immunization is carried out preferably plural times (preferably 2 to 5 times in total) at 1- to 5-week intervals, more preferably 3 times in total at 3-week intervals. One to two weeks after final administration, blood is collected from the orbit or tail vein of the immunized animal, and its serum is used to measure antibody titer. The antibody titer can be measured by methods known to those skilled in the art. Examples of such methods include radioimmunoassay (RIA), enzyme-linked immunosorbent assay (ELISA), a fluorescence antibody technique, a passive hemagglutination method, etc., and preferably is ELISA. The antibody of the present invention can be obtained by purifying from serum of the animal showing a sufficient antibody titer.

The monoclonal antibody of the present invention can be obtained by culturing hybridomas obtained by fusing a myeloma cell with an antibody-producing cell obtained from the animal immunized as described above. The fusion method includes, for example, the method of Milstein et al. (Galfre, G. & Milstein, C., Methods Enzymol. 73:3-46, 1981).

The antibody-producing cells used can be collected from the spleen, pancreas, lymph node or peripheral blood of the mouse or rat showing a sufficient antibody titer after immunization as described above, and preferably the antibody-producing cells are collected from the spleen.

The myeloma cells used are not particularly limited as long as the cells are derived from mammals such as mice, rats, guinea pigs, hamsters, rabbits or humans and can proliferate in vitro. Such cells include, for example, P3-X63Ag8 (X63) (Nature, 256, 495, 1975), P3/NS1/1-Ag4-1 (NS1) (Eur. J. Immunol., 6, 292, 1976), P3X63Ag8U1 (P3U1) (Curr. Top. Microbiol. Immunol., 81, 1, 1978), P3X63Ag8.653 (653) (J. Immunol., 123, 1548, 1979), Sp2/0-Ag14 (Sp2/O) (Nature, 276, 269, 1978), and Sp2/O/FO-2 (FO-2) (J. Immunol. Methods, 35, 1, 1980), and preferably is P3U1.

The antibody-producing cells obtained by the method described above and myeloma cells are washed with a medium, PBS (phosphate buffered saline) etc., followed by adding a cell-aggregating medium such as polyethylene glycol (hereinafter referred to as "PEG") to fuse the cells (Elsevier Publishing, 1988). The ratio of the antibody-producing cells and myeloma cells to be fused are for example 2:1 to 1:2. After cell fusion is performed, the cells are cultured in a medium such as HAT (hypoxanthine-aminopterin-thymidine) medium, thereby selectively proliferating hybridomas. After culture, the culture supernatant is recovered to select a sample binding to the antigen protein, preferably to select a sample binding to the antigen protein but not binding to a non-antigen protein, by ELISA etc. The sample is diluted to a single cell by limiting dilution, and the cell stably showing a high antibody titer can be selected to give a cell producing the monoclonal antibody.

The antibody of the present invention can be prepared by culturing the hybridoma obtained by the above described method in vitro and purifying the culture supernatant. Alternatively, the antibody of the present invention can be obtained by transplanting the hybridoma in an immunodeficient animal or in the same strain of animal which has been administered pristane intraperitoneally, thereby producing ascites in the animal, followed by purification of the recovered ascites to give the antibody of the present invention.

The antibody can be obtained by centrifugation and subsequent purification by recovery of an IgG fraction using a protein A column, a protein G column etc. When the class of the antibody is IgY or IgM, the antibody can be purified with a column with mercaptopyridine as a ligand. The antibody can, regardless of its class, be purified by using an FGFR1-immobilized column, ion-exchange chromatography, hydrophobic interaction chromatography, etc. Alternatively, the anti-FGFR1 monoclonal antibody can be obtained by antigen-specific purification (screening) by EIA using a 96-well microtiter plate having the antigen immobilized thereon.

2. Preparation of Human Chimeric Antibody, Humanized Antibody, and Human Antibody (1) Human Chimeric Antibody The human chimeric antibody of the present invention can be obtained by preparing a DNA encoding VH and VL of a nonhuman animal-derived monoclonal antibody which binds to FGFR1, ligating the DNA to a cDNA coding the constant region of a human-derived immunoglobulin, integrating the ligated DNA into an expression vector, introducing the expression vector into a suitable host cell, and expressing the DNA (Morrison, S. L. et al., Proc. Natl. Acad. Sci. USA, 81, 6851-6855, 1984).

The DNA encoding VH and VL of a nonhuman animal-derived monoclonal antibody can be obtained for example by the following method. An mRNA is extracted from animal B cells which produce the monoclonal antibody. The mRNA can be extracted by methods known by those skilled in the art, for example, by preparing RNA by a guanidine-ultracentrifugation method (Chirgwin, J. M. et al., Biochemistry 18, 5294-5299, 1979) or an AGPC method (Chomczynski, P. et al., Analytical Biochemistry, 162, 156-159, 1987), and then purifying with an mRNA purification kit (manufactured by Pharmacia or Takara Bio) or the like. From the extracted mRNA, a cDNA is prepared by using an oligo-dT primer and then integrated in a vector. From the cDNA integrated in the vector, a cDNA encoding the nonhuman animal-derived monoclonal antibody is isolated by using a part of the nonhuman animal-derived monoclonal antibody as a probe. By determining the nucleotide sequence of the isolated cDNA, the objective DNA sequence encoding VH and VL can be obtained.

As an alternative method of obtaining the DNA encoding VH and VL of a nonhuman animal-derived monoclonal antibody is as follows. The cDNA obtained by the method described above is amplified by PCR using primers capable of amplifying VH or VL (for example, a primer hybridizing with a mouse H chain constant region (C region) and a primer hybridizing with a conserved sequence of a mouse L chain gamma chain constant region when a mouse is used as a nonhuman animal (R. Orlandi et al., Proc. Natl. Acad. Sci. USA, 86, 3833, 1989)) or by extracting an mRNA from animal B cells producing the monoclonal antibody and then amplifying the VH or VL by RT-PCR with primers capable of amplifying the VH or VL. From the resulting PCR product, the objective DNA fragment is extracted. The objective DNA fragment can be extracted, for example, by cutting out a band having the size of the objective DNA after agarose gel electrophoresis, and then extracting the DNA from the gel slice. The vector and the extracted DNA are treated with restriction enzymes, then the extracted DNA is integrated in the vector, and a DNA sequence encoded by the integrated DNA is determined, whereby the DNA sequence encoding the objective VH and VL can be obtained.

Any human antibody CH and CL may be used as the human antibody CH and CL of the human chimeric antibody. Examples of the human antibody CH and CL include human gamma 1, gamma 2 CH and human kappa CL. The gene encoding the human antibody CH and CL may be chromosomal DNA or cDNA. The DNA encoding the nonhuman animal-derived monoclonal antibody VH and VL obtained as described above may be combined with a DNA encoding a human antibody CH and CL respectively to construct a vector expressing the chimeric antibody of the present invention.

An enhancer and a promoter used in expression of a human chimeric antibody include an enhancer and a promoter of an immunoglobulin gene itself and an enhancer or a promoter of a non-immunoglobulin gene. For example, when a mouse is employed as the nonhuman animal, since the mechanism of regulating expression of the immunoglobulin gene is common to both mouse and human, a recombinant DNA can be constructed in a form containing a mouse or human enhancer sequence between the J gene and the C gene.

As an animal cell expression vector, for example, pSV2-gpt (R. C. Mulligan and P. Berg, Science, 209, 1422, 1980) can be used. The genes encoding the H chain and L chain of the human chimeric antibody of the present invention constructed by the method described above may be integrated into the same vector or into different vectors.

(2) Humanized Antibody

The humanized antibody of the present invention can be obtained by constructing a DNA encoding a V region wherein an amino acid sequence encoding CDR of VH and VL of the nonhuman animal-derived monoclonal antibody binding to FGFR1 was grafted into FR of VH and VL of the human antibody, then ligating the constructed DNA to a cDNA encoding the constant region of human-derived immunoglobulin, integrating the ligated DNA into an expression vector, introducing the vector into a suitable host cell, and expressing the DNA (see L. Rieohmann et al., Nature, 332, 323, 1988; Kettleborough, C. A. et al., Protein Eng., 4, 773-783, 1991; and Clark M., Immunol. Today, 21, 397-402, 2000).

An amino acid sequence of each CDR of the nonhuman animal-derived monoclonal antibody can be obtained by comparing an amino acid sequence deduced from the DNA sequence encoding VH and VL of the nonhuman animal-derived monoclonal antibody obtained by the method described above with the whole amino acid sequence of VH and VL of a known antibody. The amino acid sequence of a known antibody can be obtained from, for example, antibody amino acid sequences registered in a database such as Protein Data Bank.

The FR of the human antibody is not particularly limited as long as the grafted antibody exhibits the effect of the present invention, and is preferably, a human antibody FR which gives a steric structure of the V region of the humanized antibody similar to the V region of the nonhuman animal-derived monoclonal antibody, or a human antibody FR having high homology with an amino acid sequence of FR of the nonhuman animal-derived monoclonal antibody used. Whether the V region of the humanized antibody having FR of the selected human antibody has a steric structure similar to the V region of the nonhuman animal-derived monoclonal antibody can be judged, for example, by predicting the steric structure of the V region of the humanized antibody by computer modeling based on DNA sequence information of the V region containing selected FR of the human antibody and then comparing the predicted steric structure with the steric structure of the V region of the nonhuman animal-derived monoclonal antibody used. The amino acid sequence of FR of the nonhuman animal-derived monoclonal antibody used can be obtained from information of an amino acid sequence predicted from the DNA sequence encoding VH and VL obtained described above, and of the amino acid sequence of CDR. The obtained amino acid sequence of FR from the human antibody may be appropriately mutated to make a human antibody FR which gives the V region of the humanized antibody similar to a steric structure of the V region of the nonhuman animal-derived monoclonal antibody or a human antibody FR having high homology with the amino acid sequence of FR of the nonhuman animal-derived monoclonal antibody used.

The DNA sequence encoding the V region of the humanized antibody used is designed as a DNA sequence corresponding to the amino acid sequence wherein the amino acid sequences of CDR of the nonhuman animal-derived monoclonal antibody are bound to the amino acid sequence of FR of the human antibody have been bound. The DNA encoding the V region of the humanized antibody can be produced based on the designed DNA by methods known to those skilled in the art. For example, the DNA encoding the V region of the humanized antibody can be obtained by chemically synthesizing a DNA fragment of 100 by or so in length as synthetic DNA based on the designed DNA, and amplifying the DNA fragment by PCR. Alternatively, the DNA encoding the V region of the humanized antibody can be obtained by binding the DNA fragments of 100 by or so in length with an enzyme such as a ligase, performing PCR using primers which encode sequences of both ends of the designed DNA sequence encoding the V region of the humanized antibody, and then extracting a DNA fragment of the desired length. Alternatively, the DNA encoding the V region of the humanized antibody used in the PCR can be obtained by the method known as CDR grafting. The DNA encoding the V region of the humanized antibody used can also be obtained by integrating the CDR-encoding DNA into the DNA of the human antibody V region by site-specific mutagenesis. The site-specific mutagenesis can be carried out by using a gene tailor site-directed mutagenesis system (Invitrogen), a transformer site-directed mutagenesis kit (Clontech), a site-directed mutagenesis system (Takara Bio) or the like according to protocols of each kit.

Any human antibody CH and CL can be used as the human antibody CH and CL of the humanized antibody. Examples include human gamma1, gamma2 CH and human kappa CL. The gene encoding the human antibody CH and CL may be chromosomal DNA or cDNA. The DNA encoding the V region of the humanized antibody obtained by the method described above can be ligated to the DNA encoding the human antibody CH and CL and then integrated in an animal cell expression vector to construct a vector expressing the humanized antibody of the present invention.

An enhancer and a promoter used in expression of the humanized antibody include an enhancer and a promoter of the immunoglobulin gene itself or an enhancer or promoter of a non-immunoglobulin gene. For example, when a mouse is employed as the nonhuman animal, since the mechanism of regulating expression of the immunoglobulin gene is common to both mouse and human, a recombinant DNA can be constructed in a form containing a mouse or human enhancer sequence between the J gene and C gene.

As an animal cell expression vector, for example, pSV2-gpt (R. C. Mulligan and P. Berg. Science, 209, 1422, 1980) can be used. The genes encoding the H chain and L chain of the humanized antibody of the present invention constructed as described above may be integrated into the same vector or into different vectors.

The nonhuman animal-derived monoclonal antibody used in preparation of the human chimeric antibody or humanized antibody is not particularly limited as long as it is an antibody binding to FGFR1, but is preferably a mouse monoclonal antibody.

(3) Human Antibody

The human antibody can be obtained by utilizing, for example, a human antibody phage library or a human antibody-producing transgenic mouse (Tomizuka et al., Nature Genet., 15, 146-156 (1997)).

The human antibody phage library is a phage library Fab, scFv etc. of human antibodies are presented on the surface of phage as fusion proteins by introducing VH gene and VL gene from an antibody gene pool having various sequences derived from human B cells into phage genes. Such human antibody phage libraries include naive nonimmune libraries (Cambridge Antibody Technology; Medical Research Council; Dyax; etc.) prepared by amplifying the VH gene and VL gene of a normal human antibody from peripheral blood lymphocytes etc. by RT-PCR or the like; synthetic libraries (BioInvent; Crucell; Morphosys; etc.) prepared by selecting a functional specific antibody gene in human B cells and then substituting the portion of an antigen-binding region such as CDR3 region of the V gene fragment with an oligonucleotide encoding a random amino acid sequence in suitable length; or immunity libraries prepared from lymphocytes of patients with cancers, patients with autoimmune diseases, patients with infections, or those persons inoculated with the objective antigen as vaccine.

For example, the naive human antibody phage library can be prepared by the following method. A mRNA is prepared from human peripheral blood and used to synthesize cDNA of V gene with primers specific to constant regions of immunoglobulin gamma, mu, kappa and lambda chains, and the respective V genes are synthesized with a set of DNA primers specific to the V gene family and then ligated the V genes by PCR via a linker DNA encoding a linker peptide such as $(Gly4Ser)_3$ to synthesize the scFv gene. The synthesized scFv gene is inserted into a phagemid vector such as pCANTAb5E by using restriction enzyme sites for introducing into a vector, and the vector is then transformed into *Escherichia coli*, followed by rescue with helper phages.

For example, when a human antibody phage library is used, the target FGFR1 is immobilized on a solid phase, then reacted with the phage antibody library, washed to remove unbound phages, and bound phages are recovered whereby desired clones can be obtained (panning). The accuracy of the resulting clones can further be increased by amplifying the obtained phages, and panning repeatedly the amplified library. By analyzing the VH gene and VL gene of the resulting clones, the complete human antibody having these gene sequences can be prepared.

A human antibody-producing transgenic mouse is an endogenous immunoglobulin (Ig) gene being knocked out mouse into which a human antibody Ig gene is introduced. The human antibody-producing transgenic mouse can be obtained for example by the following method. Human-mouse hybrid cells are treated with colcemid (a spindle formation inhibitor) for 48 hours, to form a microcell that is a structure having 1 to several chromosomes enclosed by a nuclear membrane. The microcell isolated in the presence of cytochalasin B is fused with a chromosome-receiving cell (mouse ES cell) by polyethylene glycol, to prepare a microcell hybrid ES cell, which is then injected into a mouse embryo.

The anti-FGFR1 human antibody can be obtained by immunizing the human antibody-producing transgenic mouse with the antigen in accordance with the method of preparing the anti-FGFR1 antibody as described above.

3. Preparation of Antibody Fragments

Fragments of the antibody of the present invention ($F(ab')_2$, Fab', Fab, scFv, dsFv and a polymer thereof, a diabody, and a CDR-containing peptide) can be prepared by the following method.

The $F(ab')_2$ fragment of the present invention can be obtained as an antibody fragment with a molecular weight of about 100,000 having an antigen binding activity by cleaving the FGFR1-binding IgG antibody of the present invention at position 234 of the amino acid residue in the H chain by treatment with a protease pepsin. The $F(ab')_2$ fragment of the present invention can be obtained by binding Fab' fragments described below via a thioether linkage or a disulfide linkage.

The Fab' fragments of the present invention can be obtained by treating the FGFR1-binding $F(ab')_2$ in the present invention obtained by the method described above with a reducing agent dithiothreitol. The Fab' fragment of the present invention also can be obtained by inserting the DNA encoding Fab' of the antibody binding to the FGFR1 of the present invention, into an expression vector, introducing the vector into a host cell, and expressing the DNA.

By treating the FGFR1-binding antibody of the present invention with a proteinase papain to cleave the antibody at position 224 of the amino acid residue in the H the Fab fragment of the present invention can be obtained as an antibody fragment with a molecular weight of about 50,000 having an antigen binding activity, which consists of about half of the N-terminal side of H chain and the whole region of L chain which are bound via a disulfide linkage. The Fab fragment of the present invention can be obtained by inserting, into an expression vector, the DNA encoding Fab of the antibody binding to FGFR1 of the present invention, introducing the vector into a host cell, and expressing the DNA.

The scFv of the present invention can be obtained by acquiring cDNAs coding for VH and VL of the antibody binding to FGFR1 of the present invention, inserting a DNA encoding a linker sequence between the genes to construct a DNA encoding scFv, inserting the DNA into an expression vector, introducing the vector into a host cell, and expressing the DNA. The length of the linker is not particularly limited as long as the linker has a length to enable association of VH with VL, and is preferably 10 to 20 bases, more preferably 15 bases. The sequence of the linker is not particularly limited as long as it does not inhibit the polypeptide-chain folding of two domains VH and VL, and preferably consists of glycine and/or serine, and more preferably is GGGGS (G: glycine, S: serine) or a repeating sequence thereof.

The dsFv of the present invention can be obtained by substituting one amino acid residue in VH and VL with a cysteine residue by site-specific mutagenesis and then binding VH and VL via a disulfide bond at the cysteine residues. The amino acid to be substituted is not particularly limited as long as it is an amino acid residue which does not influence the antigen binding based on its steric structure.

The diabody of the present invention can be obtained by constructing the DNA which encodes the scFv as described above with 8 residues or less (preferably 5 residues) of the amino acid sequence, then inserting the DNA into an expression vector, introducing the vector into a host cell, and expressing the DNA. The bi-specific diabody can be obtained by ligating two different kinds of scFv VH and VL DNAs in preparing scFv.

The CDR-containing peptide of the present invention can be obtained by constructing a DNA encoding an amino acid sequence of CDR in VH or VL of the antibody binding to FGFR1 of the present invention, then inserting the DNA into an expression vector, introducing the vector into a host cell, and expressing the DNA.

The peripheral blood mononuclear cell of the present invention can be collected by methods known to those skilled in the art, such as a density gradient centrifugation method. For example, collected blood is diluted twofold with PBS, and then 6 mL of the resulting dilution is overlaid gently on a lymphocyte separating liquid (3 mL) and then centrifuged at 1500 rpm for 30 minutes. Peripheral blood mononuclear cells consisting of lymphocytes and monocytes are observed as a white zonal layer between plasma (with a yellowish tone) and a separated liquid (transparent). The white zonal mononuclear cell layer (cell suspension) is recovered by suctioning into a Pasteur pipette. After PBS is added, the recovered cell suspension is stirred and then centrifuged at 1500 rpm for 10 minutes. After the centrifugation, the supernatant is removed, and 10 mL PBS is added to the cell pellet, to suspend the cells which are then centrifuged at 1500 rpm for 10 minutes. After the centrifugation, the supernatant is removed, and the cell pellet can be suspended in PBS to give a peripheral blood mononuclear cell suspension.

In the agent or method of the present invention, one kind of FGFR1 expression enhancer may be used, or two or more kinds of FGFR1 expression enhancers may be used in suitable combination. The amount of the FGFR1 expression enhancer to be administered in the agent or method of the present invention can be determined appropriately depending on the type of cancer, the ability of the FGFR1 expression agent to express FGFR1, the degree of symptoms of the patient, the age and sex of the patient, the dosage form of the preparation used, and the like. For example, when IFN-alpha is used as the FGFR1 expression enhancer, the amount of the enhancer to be administered once can be for example 5,000,000 to 10,000,000 units. When IFN-beta is used as the FGFR1 expression enhancer, the amount of the enhancer to be administered once can be for example 3,000,000 to 6,000,000 units. When adriamycin or 5-azacitidine are used, the amount of the enhancer to be administered once can be for example in the range of 0.01 to 10 mg/kg (for example, 0.4 mg/kg) and in the range of 1 to 100 mg/m$^2$ (for example, 15 mg/m$^2$). The FGFR1 expression enhancer can be administered once to five times (preferably once to several times) per day, all at once or continuously.

In the agent or method of the present invention, one kind of anti-FGFR1 antibody or a fragment thereof may be used, or two or more kinds of anti-FGFR1 antibodies or their fragments may be used in suitable combination. The amount of the anti-FGFR1 antibody or a fragment thereof to be administered can be determined appropriately depending on the degree of symptoms of the patient, the age, sex and weight of the patient, the dosage form of the preparation used, the binding titer of the antibody, and the like. For example, the antibody or a fragment thereof may be administered once in a dose of about 100 to 200 mg. Administration can be performed once to five times (preferably once to several times) per day, all at once or continuously.

The amount of the peripheral blood mononuclear cells to be administered in the agent or method of the present invention varies depending on the degree of symptoms of the patient, the age, sex and weight of the patient, the state and origin of the cells to be administered, the distribution of each kind of cell contained in the peripheral blood mononuclear cells, etc., but may be usually $1 \times 10^5$ to $1 \times 10^9$ cells per administration or $1 \times 10^5$ to $1 \times 10^9$ cells per administration.

The therapeutic agent of the present invention is prepared by further purifying the FGFR1 expression enhancer (IFN-alpha, IFN-beta) and the anti-FGFR1 antibody as necessary and then forming them into a single pharmaceutical preparation or separate pharmaceutical preparations by a conventional method. In preparation of the therapeutic agent of the present invention, carriers and additives (see "Iyakuhin Tenkabutsu Jiten" (Medicinal Additive Dictionary) published by Yakuji Nippo Limited and "Handbook of Pharmaceutical Excipients" published by APhA Publications) can be used in a pharmaceutically acceptable range. The dosage form of the therapeutic agent of the present invention includes, for example, an injection, capsules, tablets, syrup, granules etc. When the peripheral blood mononuclear cells are administered in the method of the present invention, the peripheral blood mononuclear cells can be used in a state suspended in a suspension that can be administered appropriately to the living body by a method known to those skilled in the art.

The administration route of the agent of the present invention includes oral administration, intraoral administration, intratracheal administration, subcutaneous administration, intramuscular administration, and intravascular (intravenous) administration. The method of administering the agent of the present invention is not particularly limited, and examples include a subcutaneous or intravenous administration by a syringe or by drip infusion and an arterial administration via a catheter. Specifically, IFN-alpha is preferably subcutaneously injected with a syringe, and IFN-beta, adriamycin, 5-azacitidine or the anti-FGFR1 antibody is preferably intravenously injected by drip infusion. When the peripheral blood mononuclear cells are administered in the method of the present invention, the administration may be carried out intravascular (intravenous) administration.

In the method of the present invention, the administration interval of the agent of the present invention is not particularly limited as long as its therapeutic effect can be obtained. For example, the FGFR1 expression enhancer and the anti-FGFR1 antibody can be administered simultaneously, continuously, or separately at an interval. For example, when the FGFR1 expression enhancer and the anti-FGFR1 antibody are to be simultaneously administered, the FGFR1 expression enhancer and the anti-FGFR1 antibody may be simultaneously administered in the same pharmaceutical preparation to a cancer patient. When the FGFR1 expression enhancer and the anti-FGFR1 antibody are to be administered at an interval, the FGFR1 expression enhancer (for example, IFN-alpha or IFN-beta) is first administered to a cancer patient, and after elapse of a time to permit enhancement of specific expression of FGFR1 in cancer cells, the anti-FGFR1 antibody or a fragment thereof is administered, whereby the FGFR1 which expression has been enhanced can bind to the anti-FGFR1 antibody or a fragment thereof. Specifically, the FGFR1 expression enhancer (IFN-alpha or IFN-beta) is administered to a cancer patient and 32 to 48 hours after administration the anti-FGFR1 antibody is administered which is regarded as one cycle, and the two cycles are conducted per week.

When the peripheral blood mononuclear cells are administered in the method of the present invention, the peripheral blood mononuclear cells may be administered simultaneously with the FGFR1 expression enhancer and/or the anti-FGFR1 antibody, or continuously, or separately at an interval.

EXAMPLES

Hereinafter, the present invention will be described in more detail with reference to the examples, but the present invention is not limited to these examples.

Example 1

Administration of IFN to a SCID Mouse Xenografted with Hepatic Cancer Cell Line HepG2

DNA Array Analysis

A hepatic cancer cell line HepG2 ($1 \times 10^6$ cells) was xenografted in one severe combined immunodeficient (SCID) mouse. Three weeks after xenografting when the tumor in the mouse reached about 6 to 7 mm in size, IFN-alpha (OIF, manufactured by Otsuka Pharmaceutical Co., Ltd.) was administered intravenously twice in a dose of 2000 U/mouse. Before and 24 hours after administration of INF-alpha, tumor tissues were collected.

From the collected tumor tissues, RNA was extracted with trizol (manufactured by Invitrogen) and converted into cDNA by Superscript III (manufactured by Invitrogen). Thereafter, the cDNA was reacted using Gene Navigator cDNA Array Filter—human cancer (manufactured by Toyobo) and subjected to DNA array analysis with Fluor-S Multi Imager (manufactured by Bio-Rad).

The result of DNA array analysis is shown in FIG. 1. The obtained signal intensities corrected with a control value are shown in Table 1. As a result, it was revealed that the specific expression of FGFR1 gene in the hepatic cancer cells was strongly induced by administering IFN-alpha.

| Gene | Fluorescence Intensity of Each Gene | |
|---|---|---|
| | Before Administration | 24 Hours after Administration |
| FGFR1 | 3293 | 30992 |
| FGFR2 | 614.5 | 332 |
| FGFR3 | 703.5 | 34 |
| FGFR4 | 1400 | 1875 |

Example 2

Preparation of Anti-FGFR1 Antibody (1) Preparation of Immunizing Antigen (Expression Vector)

A polynucleotide corresponding to the region from position 1 to position 822 in the whole amino acid sequence of FGFR1 represented by SEQ ID NO: 1 was amplified by polymerase chain reaction (PCR) using full-length FGFR1 (Accession No. NM_000604) as a template and primer No. 5'-3 and primer No. 3'-3 shown below. Then, the polynucleotide obtained above was inserted into pcDNA3.1 (manufactured by Invitrogen) to construct an expression vector.

```
Primer No. 5'-3 (SEQ ID NO: 3):
5'-ACGGGATCCAGGACCCTGGCTGGAGAGACA-3'

Primer No. 3'-3 (SEQ ID NO: 4):
5'-AAGCTCGAGCCGCCGGAACCGCGGCCGGA-3'
```

(2) Preparation of Monoclonal Antibody (Immunization with Expression Vector)

The expression vector obtained by the method of above (1) was administered as the immunizing antigen in a dose of 50 micro L (50 micro g) at 1 or 2 week intervals to immunize a mouse. The antigen for initial immunization was admixed with complete Freund's adjuvant and the antigens for second and subsequent administration were admixed with incomplete Freund's adjuvant. Spleen monocytic cells from the immunized mouse and a fusion partner X63-Ag8-653 were fused by polyethylene glycol-mediated cell fusion, followed by selection of a hybridoma by a method described in a literature (J. Immunol. 146:3721-3728). Cells that had reacted with the immobilized FGFR1 were selected. The cells selected as described above were cultured in a serum-free GIT medium (Wako Pure Chemical Industries, Ltd.) to produce antibodies until 80% of the cells perished. Next, the cells were removed from this medium by centrifugation (1,000 rpm, 15 minutes), then the medium was 50% saturated by ammonium sulfate and left overnight at 4° C., and precipitates were recovered by centrifugation (1,000 rpm, 30 minutes). The precipitates were dissolved in a twofold diluted binding buffer (manufactured by Protein AMAPS II kit), and the IgG was adsorbed on a protein A column (manufactured by Pharmacia-Amersham). Thereafter, dialysis against PBS was performed overnight to purify antibodies, whereby a plurality of antibodies recognizing FGFR1 were obtained. One of these antibodies was designated A2C9-1.

(3) Confirmation of Specificity of Monoclonal Antibody A2C9-1 by Western Blotting The monoclonal antibody A2C9-1 obtained by the method of above (2) was confirmed to recognize FGFR1 by western blotting with samples such as FGFR1 protein etc. forced expressed in NIH3T3 cells. Each sample was reduced by adding 2-mercaptoethanol (2-Me) before western blotting. The western blotting was performed in accordance with the conventional method (for example, "Bunshi Seibutsugaku Kiso Jikken-Ho" (Basic Experimental Method in Molecular Biology), Nankodo Co., Ltd.).

Figure 2:
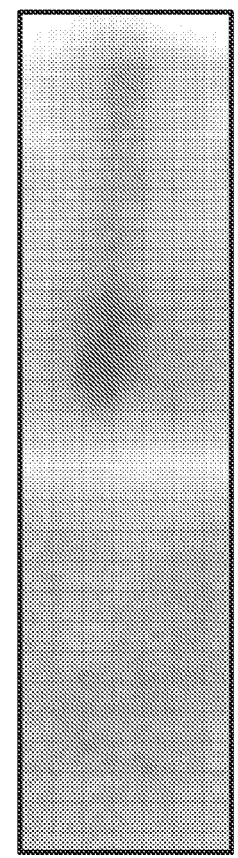
FIG. 2 shows a result of a specificity test by western blotting with the anti-FGFR1 antibody (lane 2 shows a lysate of NIH3T3 cells into which the full-length FGFR1 cDNA was introduced, and lane 1 shows a lysate of NIH3T3 cells into which the gene was not introduced).

The result of western blotting is shown in FIG. 2. According to FIG. 2, it was confirmed that the monoclonal antibody A2C9-1 showed a band at the expression site of FGFR1 in the FGFR1 forced expressed sample, and that the antibody have reactivity to FGFR1. Hereinafter, the monoclonal antibody A2C9-1 is referred to as anti-FGFR1 antibody.

Example 3

Enhancement of FGFR1 Expression at Protein Level in Hepatic Cancer Cell Line by Administering IFN (1)

Figure 3:
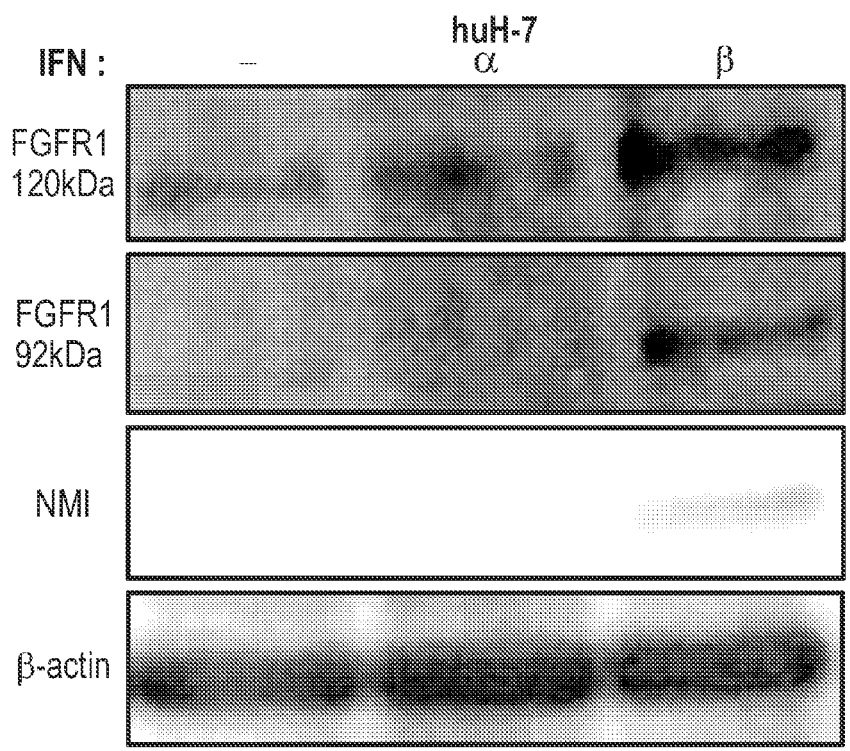
FIG. 3 shows a result of western blotting analysis, wherein FGFR1 expression in a hepatic cancer cell line was enhanced at protein level by administering IFN.

1,000 IU/ml of IFN-alpha or IFN-beta was administered to a hepatic cancer cell line huH-7. 48 hours after administration, a change of FGFR1 was examined by western blotting. The results are shown in FIG. 3. From this profile, the expression level of FGFR1 at the protein level was increased by administering IFN-alpha or IFN-beta.

Example 4

Enhancement of FGFR1 Expression at Protein Level in Hepatic Cancer Cell Line by Administering IFN (2)

Figure 4:
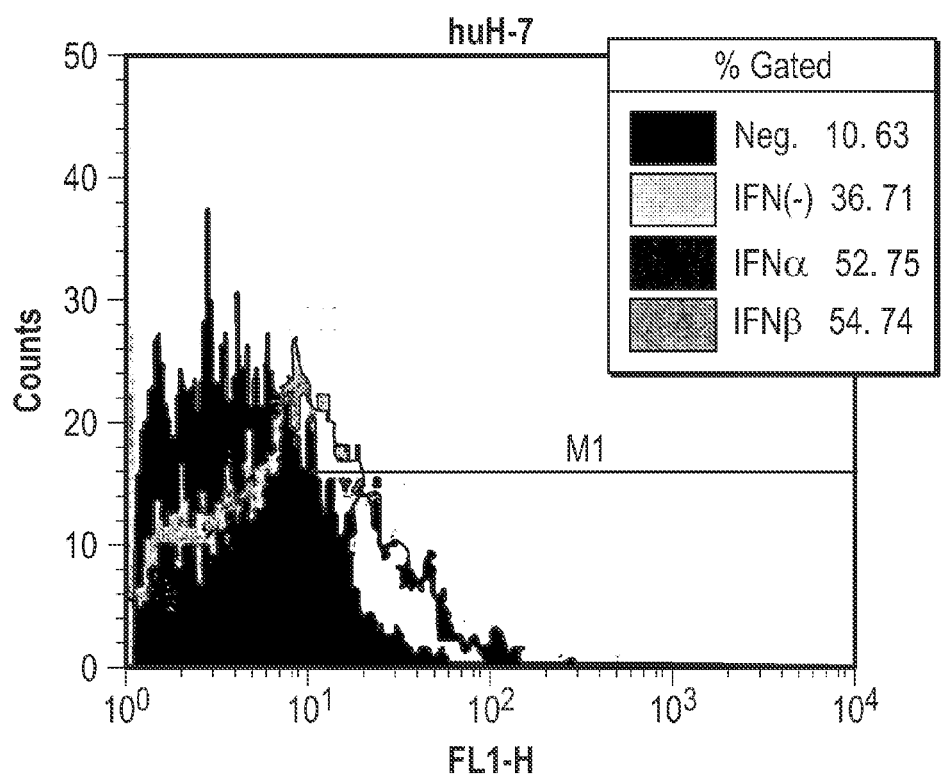
FIG. 4 shows a result of FACS analysis, wherein an FGFR1 expression on the surface of a hepatic cancer cell line was enhanced by administering IFN.

1,000 IU/ml of IFN-alpha or IFN-beta was administered to a hepatic cancer cell line huH-7. 48 hours after administration, a change of FGFR1 was examined by FACS. The results are shown in FIG. 4. As shown in the graph, similarly to the western blotting analysis, FACS analysis revealed that the expression level of FGFR1 was increased by administering IFN-alpha or IFN-beta.

Example 5

Figure 5A:
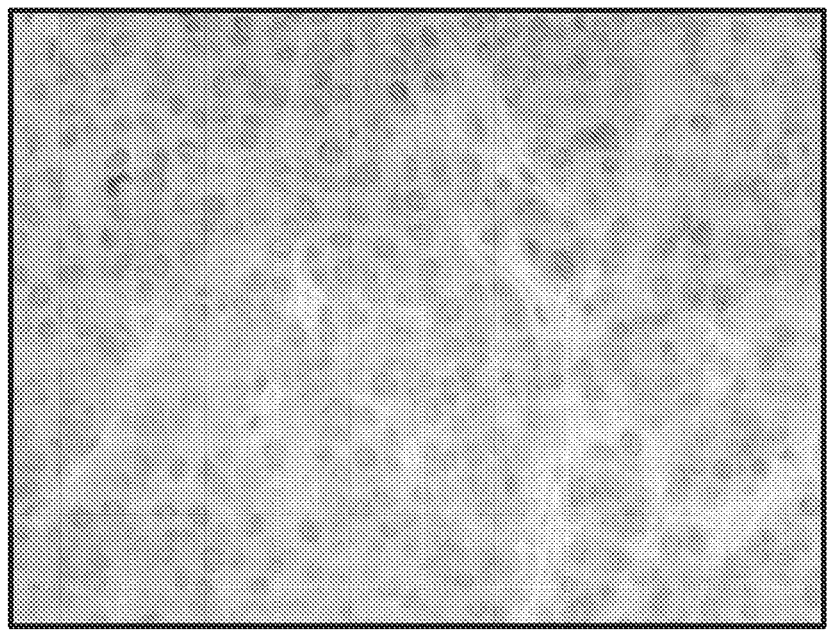
FIG. 5 shows a result of immunohistological analysis of FGFR1 expression after administration of IFN-alpha in a excised piece from a SCID mouse which had been xenografted hepatic cancer cell line HepG2.
Figure 5B:
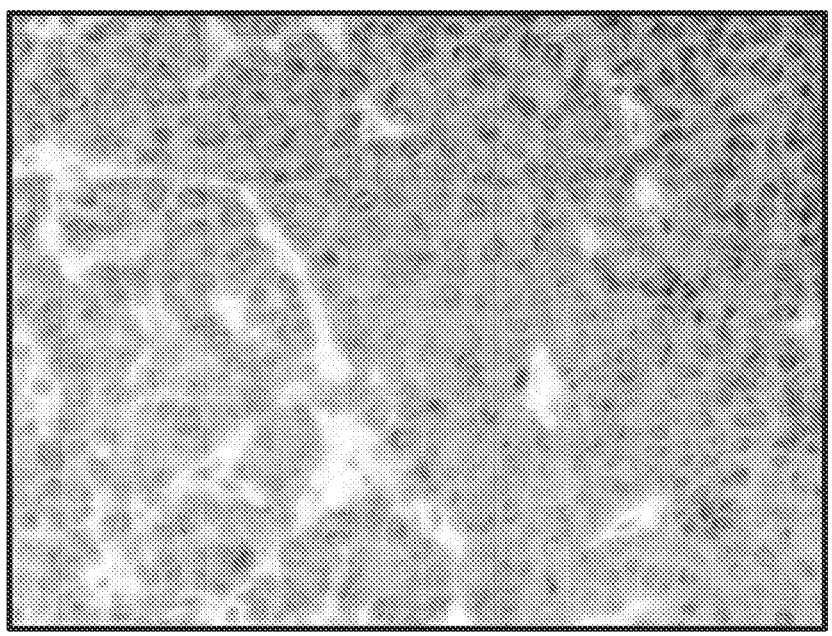

Analysis of Expression of FGFR1 in Excised Piece from Hepatic Cancer Cell Line-Xenografted Mouse HepG2 ($1 \times 10^6$ cells) was xenografted in an SCID mouse. When the tumor in the mouse reached 10 mm, IFN-alpha (OIF, manufactured by Otsuka Pharmaceutical Co., Ltd.) was administered in a dose of 100 U/g, and 24 hours after administration, tumor tissues were collected and stained with an anti-hFGFR1 antibody (sc-121, manufactured by Santa Cruz). The results are shown in FIG. 5. From the photographs, it was confirmed that FGFR1 is expressed more strongly after administration of IFN-alpha than before administration of IFN-alpha.

Example 6

Growth Inhibition of Hepatic Cancer Cell Line by Anti-FGFR1 Antibody

Figure 6A:
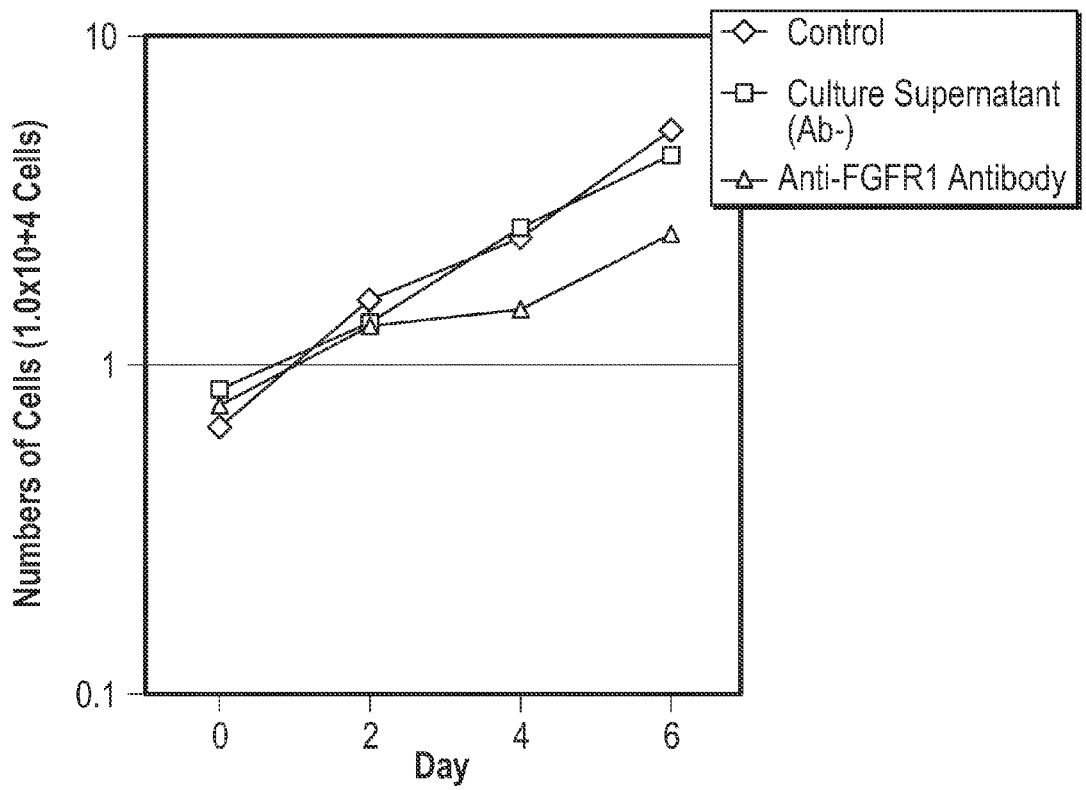
FIG. 6 shows a growth inhibition of a hepatic cancer cell line by the anti-FGFR1 antibody.
Figure 6B:
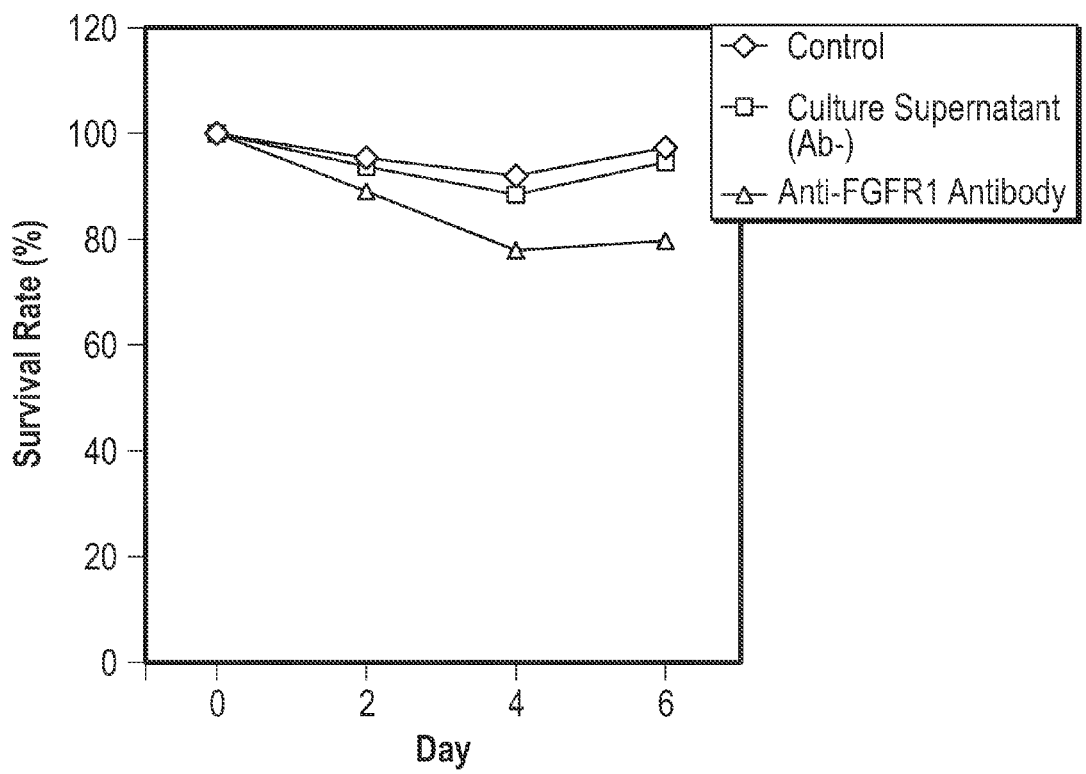
Figure 7A:
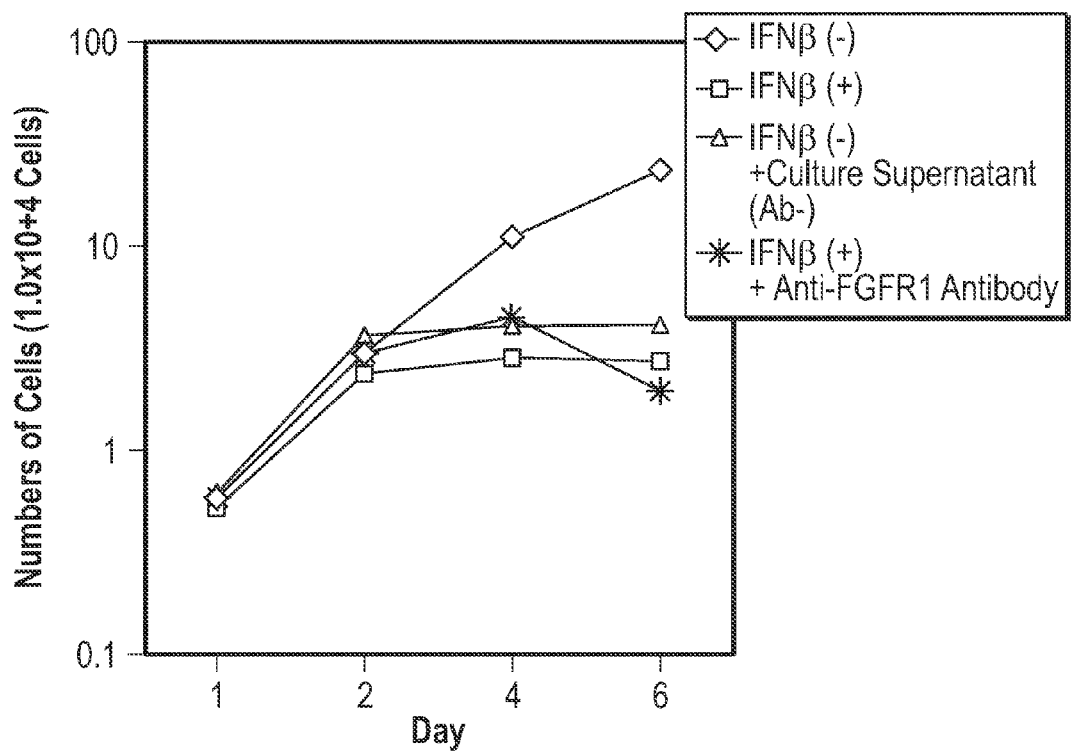
FIG. 7 shows a growth inhibition of a hepatic cancer cell line by IFN-beta and the anti-FGFR1 antibody.
Figure 7B:
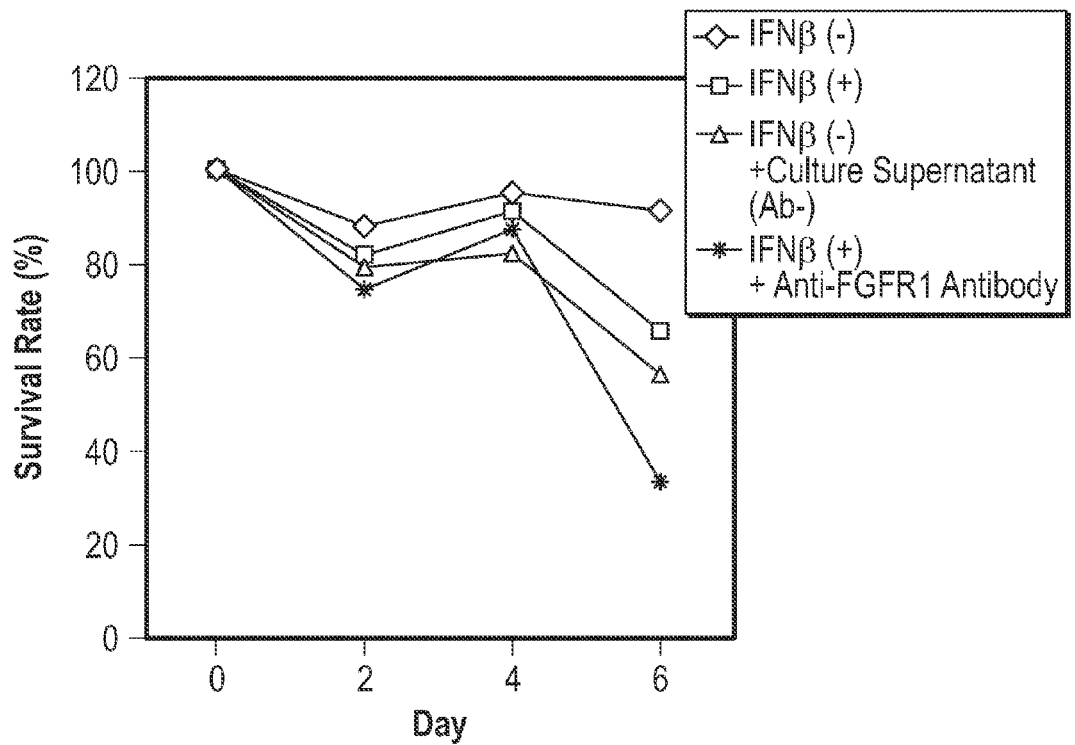

To examine the influence of administration of IFN-beta and the anti-FGFR1 antibody on a hepatic cancer cell line, the proliferation and survival rate of a hepatic cancer cell line were examined in the presence of IFN-beta (Feron, manufactured by Toray) and the anti-FGFR1 antibody. First, $1.0 \times 10^4$. huH-7 cells were seeded to each well of a 24-well plate, then the anti-FGFR1 antibody prepared in Example 2 or an antibody-free culture supernatant as a negative control was added. Cells to which nothing was added were used as control. Then the cells were cultured for 0 to 6 days. Thereafter, the cells were detached with trypsin, and the number and survival rate of cells were measured. The results are shown in FIG. 6. From this graph, inhibition of the cell growth and decrease in the survival rate were confirmed in the case that only the anti-FGFR1 antibody was added in the absence of IFN-beta. The result of addition of IFN-beta in the same experiment is shown in FIG. 7. From this graph, inhibition of the cell growth and decrease in the survival rate were observed in the case that IFN-beta was added alone. However, by adding the anti-FGFR1 antibody in addition to IFN-beta, the survival rate was about 40% lowered compared to the case anti-FGFR1 antibody was not administered.

Example 7

Therapeutic Experiment with Human Hepatic Cancer Cell-Xenografted Mouse

Human hepatic cancer-derived cell line HepG2 ($5 \times 10^6$ cells) was xenografted subcutaneously in the back of a CB17-scid/scid mouse. When the tumor volume reached 100 mm$^3$, the anti-FGFR1 antibody, the peripheral blood mononuclear cell, and a chemical were administered as follows:

PBS administration group: intraperitoneal injection of PBS (250 micro L)/normal mouse IgG (100 micro g)/mouse IFN-alpha administration group: intraperitoneal injection of IFN-alpha (OIF: 4000 U)/normal mouse IgG (100 micro g)/mouse Antibody alone administration group: intravenous injection of PBS/anti-FGFR1 antibody (100 micro g)/mouse IFN-alpha+antibody administration group: intraperitoneal injection and intravenous injection of IFN-alpha/anti-FGFR1 antibody (each in equal amount)

Figure 8:
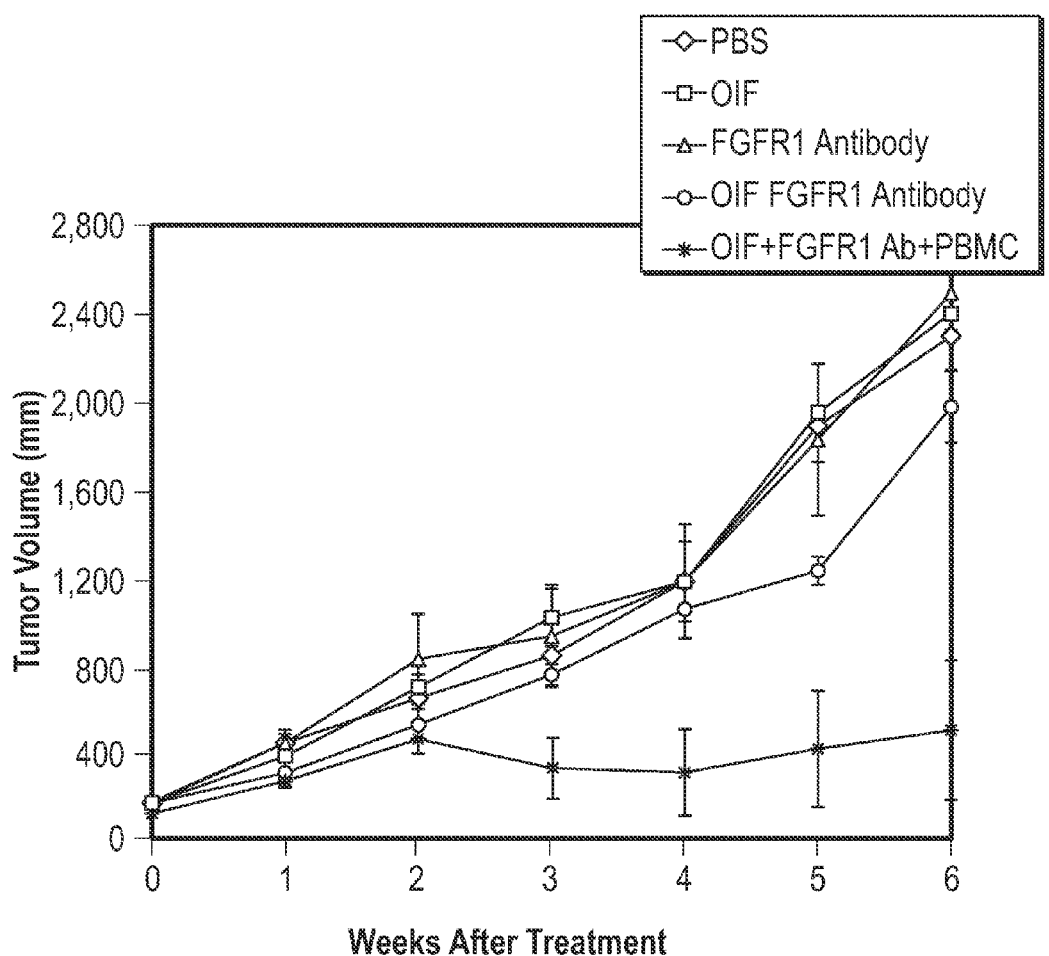
FIG. 8 is a graph showing a change of the size of hepatic cancer by administering IFN-alpha, the anti-FGFR1 antibody, or IFN-alpha+anti-FGFR1 antibody to a hepatic cancer-xenografted SCID mouse. In the graph, the size of hepatic cancer is shown on the vertical axis, and the elapsed time after administration of each drug is shown on the horizontal axis.

IFN-alpha+antibody+peripheral blood mononuclear cell administration group: intraperitoneal injection and intravenous injection of IFN-alpha/anti-FGFR1 antibody (each in equal amount) and further intravenous administration of PBMNCs ($1 \times 10^7$ cells)/mouse Administration was conducted 5 times in total on day 0 as first administration day, then 1 week later (w1), 2 weeks later (w2), 5 weeks later (w5) and 6 weeks later (w6). Only at w6, 200 micro g/mouse was administered. Each group consisted of 4 animals, and the size of tumor was measured as ((major axis×(minor axis)$_2$)/2) at every week after initial administration. The results are shown in FIG. 8. "PBS" represented as diamond shape indicates the control group, "IFN-alpha" represented as square indicates the IFN-alpha administration group, "FGFR1 antibody" shown by triangle shape indicates the anti-FGFR1 antibody administration group, and "IFN-alpha+FGFR1 antibody" shown by cross mark indicates the group administered with both IFN-alpha and anti-FGFR antibody. As shown in FIG. 8, the group administered with only the antibody and the group administered with only IFN-alpha showed no difference from the control group, on the other hand the group administered with both IFN-alpha and the antibody evidently showed an inhibitory effect on tumor growth. In the group further administered with the peripheral blood mononuclear cells, a significant antitumor effect, including disappearance of the tumor in 2 of 4 animals, was observed.

From the Examples above, it was revealed that IFN-alpha or IFN-beta enhances the expression of FGFR1 in the hepatic cancer cell line. Growth and survival of the hepatic cancer cells whose FGFR1 expression had been enhanced were significantly inhibited by the anti-FGFR1 antibody. Further-more, the result of the examination using the peripheral blood mononuclear cells showed that further effect in the human body can be expected.

Example 8

Figures 9, 10:
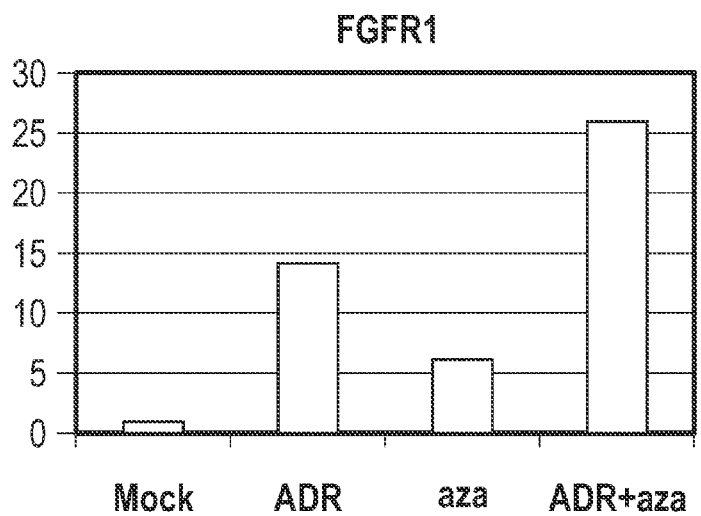
FIG. 9 shows as enhancement of FGFR1 expression on the surface of a hepatic cancer cell line by administering IFN detected by FACS.
FIG. 10 shows a change of expression of FGFR1 at the mRNA level in multiple myeloma cell line KMS12BM by administering ADR and/or decitabine. In the graph, the expression change in fold relative to the control (non-administration group) is shown on the vertical axis, which assumes that the expression of the control (non-administration group) is 1. In the graph, Aza on the abscissa means horizontal axis.

Enhancement of Expression of FGFR1 at Protein Level in Cell lines of Hepatic Cancer, Gallbladder Cancer, Myeloma, Colon Cancer, Stomach Cancer, Breast Cancer, Leukemia and Pancreas Cancer by Administering IFN $1 \times 10^6$ cells each of hepatic cell lines HepG2 and huH-7, hepatic cancer (gallbladder cancer) cell line CHC4, myeloma cell line RPMI8226, colon cancer cell line HCT116, stomach cancer cell lines MKN-45, MKN-74, and SH101, breast cancer cell lines MDA-MB-4355 and MRK-nut, leukemia cell line U937, and pancreas cancer cell line HPC-yo were seeded on a 100-mm$^2$ plate, and IFN-alpha (Otsuka Pharmaceutical Co., Ltd.), IFN-beta (Toray) or IFN-gamma (only for the hepatic cancer cell line) were added in an amount of 1,000 IU/ml respectively, and the cells were cultured in 5% $CO_2$ at 37° C. for 48 hours. After culture, a change of FGFR1 was analyzed by FACS using 20 micro g/mL anti-FGFR1 monoclonal antibody M19B2 (Catalog No. 30101, QED Bioscience) as a primary antibody and 25 micro g/mL anti-mouse IgG+M-FITC (Catalog No. 17621, Immuno-Biological Laboratories) as a second antibody. Dox40 cells were used as antibody-positive control cells, and jurkat cells were used as antibody-negative control cells. The results are shown in FIG. 9. From this result, it was confirmed that even in the cancer cells other than the hepatic cancer, the expression level of FGFR1 is increased by stimulation with IFN.

Example 9

Enhancement of FGFR1 Expression at mRNA Level in Multiple Myeloma Cell Line KMS12BM by Administering ADR and/or Decitabine Using a DNA array, 1 micro M decitabine and/or 0.5 micro g/mL ADR was administered to KMS12BM cells and a change in expression of FGFR1 at the mRNA level was examined 72 hours after administration of decitabine and 24 hours after administration of ADR. The results are shown in FIG. 10. In the graph, the expression level ratio relative to the expression level in the cell line to which no drug was administered is shown on the vertical axis. In the graph, the decitabine administration group is shown by Aza. From this result, the expression level of FGFR1 was increased by stimulation with ADR and/or decitabine.

This application claims priority of Japanese Patent Application No. 2007-142308 filed May 29, 2007, which is hereby incorporated by reference in its entirety. The entire contents of all documents cited in this specification are incorporated herein by reference.

Industrial Applicability

The agent for treatment of hepatic cancer according to the present invention influences the growth and survival of only hepatic cancer cells without influencing normal hepatocytes and can thus be used in treatment of hepatic cancer.

The invention claimed is:

1. A composition for treatment of hepatic cancer, gallbladder cancer, colon cancer, stomach cancer, breast cancer, pancreas cancer, myeloma, or leukemia, comprising a fibroblast growth factor receptor-1 (FGFR-1) expression enhancer which is interferon-alpha, interferon-beta, or 5-azacitidine and an anti-FGFR-1 antibody or a fragment thereof that binds to FGFR-1,
wherein the dosage of interferon-alpha is 5,000,000-10,000,000 units, the dosage of interferon-beta is 3,000,000-6,000,000 units, the dosage of 5-azacitidine is 0.01-10 mg/kg and the dosage of said antibodies is 100-200 mg.

2. The composition of claim 1 which further comprises peripheral blood mononuclear cells.

3. The composition of claim 1, wherein the anti-FGFR-1 antibody or fragment thereof is bound to an anticancer drug.

4. The composition of claim 3, wherein the anticancer drug is an anticancer drug-containing targeting liposome.

5. A method for treatment of cancer, comprising administering to a subject in need of such treatment an effective amount of a composition comprising an agent that enhances the expression of fibroblast growth factor receptor-1 (FGFR-1) on cancer cells in said subject which agent is interferon-alpha, interferon-beta, or 5-azacitidine and further administering an effective amount of an anti-FGFR-1 antibody or a fragment thereof that binds to FGFR-1;
wherein the cancer is hepatic cancer, gallbladder cancer, colon cancer, stomach cancer, breast cancer, pancreas cancer, myeloma, or leukemia,
wherein the dosage of interferon-alpha is 5,000,000-10,000,000 units, the dosage of interferon-beta is 3,000,000-6,000,000 units, the dosage of 5-azacitidine is 0.01-10 mg/kg and the dosage of said antibodies is 100-200 mg.

6. The method of claim 5, further comprising administering to said subject peripheral blood mononuclear cells.

7. A method for treatment of cancer in a subject in need thereof, comprising administering to said subject an effective amount of an FGFR-1 expression enhancer which enhancer is interferon-alpha, interferon-beta, or 5-azacitidine and an effective amount of an anti-FGFR-1 antibody or a fragment thereof that binds to FGFR-1 in amounts effective to treat said cancer;
wherein the cancer is hepatic cancer, gallbladder cancer, colon cancer, stomach cancer, breast cancer, pancreas cancer, myeloma, or leukemia,
wherein the dosage of interferon-alpha is 5,000,000-10,000,000 units, the dosage of interferon-beta is 3,000,000-6,000,000 units, the dosage of 5-azacitidine is 0.01-10 mg/kg and the dosage of said antibodies is 100-200 mg.

8. The method of claim 7, further comprising administering to said subject peripheral blood mononuclear cells.

9. The method of claim 7, wherein said enhancer and antibody or fragment are administered simultaneously.

10. The method of claim 7, wherein the anti-FGFR-1 antibody or fragment thereof is bound to an anticancer drug.

11. The method of claim 10, wherein the anticancer drug is a cellular toxin or a targeting liposome.

12. A method for inhibiting growth of hepatic cancer cells in a subject, which method comprises administering to a subject in need of such treatment interferon-alpha, interferon-beta, or 5-azacitidine to said subject followed by administering an anti-FGFR-1 antibody or a fragment thereof that binds to FGFR-1, thereby inhibiting growth of said hepatic cancer cells, wherein the dosage of interferon-alpha is 5,000,000-10,000,000 units, the dosage of interferon-beta is 3,000,000-6,000,000 units, the dosage of 5-azacitidine is 0.01-10 mg/kg and the dosage of said antibodies is 100-200 mg.

13. The method of claim 7, wherein said enhancer and antibody or fragment are administered continuously.

14. The method of claim 7, wherein said enhancer and antibody or fragment are administered separately at one or more intervals.

15. A method for treatment of hepatic cancer, gallbladder cancer, colon cancer, stomach cancer, breast cancer, pancreas cancer, myeloma, or leukemia, comprising administering to a subject in need thereof an effective amount of the composition of claim 2.

16. A method for treatment of hepatic cancer, gallbladder cancer, colon cancer, stomach cancer, breast cancer, pancreas cancer, myeloma, or leukemia, comprising administering to a subject in need thereof an effective amount of the composition of claim 3.

17. A method for treatment of hepatic cancer, gallbladder cancer, colon cancer, stomach cancer, breast cancer, pancreas cancer, myeloma, or leukemia, comprising administering to a subject in need thereof an effective amount of the composition of claim 4.

* * * * *

SEQUENCE LISTING

```
<160> NUMBER OF SEQ ID NOS: 4

<210> SEQ ID NO 1
<211> LENGTH: 822
<212> TYPE: PRT
<213> ORGANISM: Homo sapiens
<300> PUBLICATION INFORMATION:
<308> DATABASE ACCESSION NUMBER: NM_023110
<309> DATABASE ENTRY DATE: 2007-03-01
<313> RELEVANT RESIDUES IN SEQ ID NO: (1)..(822)

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
            115                 120                 125
```

-continued

Asp Asp Asp Asp Asp Ser Ser Ser Glu Glu Lys Glu Thr Asp Asn Thr
130                 135             140

Lys Pro Asn Arg Met Pro Val Ala Pro Tyr Trp Thr Ser Pro Glu Lys
145             150             155             160

Met Glu Lys Lys Leu His Ala Val Pro Ala Lys Thr Val Lys Phe
        165             170             175

Lys Cys Pro Ser Ser Gly Thr Pro Asn Pro Thr Leu Arg Trp Leu Lys
            180             185             190

Asn Gly Lys Glu Phe Lys Pro Asp His Arg Ile Gly Tyr Lys Val
        195             200             205

Arg Tyr Ala Thr Trp Ser Ile Ile Met Asp Ser Val Val Pro Ser Asp
    210             215             220

Lys Gly Asn Tyr Thr Cys Ile Val Glu Asn Glu Tyr Gly Ser Ile Asn
225             230             235             240

His Thr Tyr Gln Leu Asp Val Val Glu Arg Ser Pro His Arg Pro Ile
            245             250             255

Leu Gln Ala Gly Leu Pro Ala Asn Lys Thr Val Ala Leu Gly Ser Asn
            260             265             270

Val Glu Phe Met Cys Lys Val Tyr Ser Asp Pro Gln Pro His Ile Gln
    275             280             285

Trp Leu Lys His Ile Glu Val Asn Gly Ser Lys Ile Gly Pro Asp Asn
    290             295             300

Leu Pro Tyr Val Gln Ile Leu Lys Thr Ala Gly Val Asn Thr Thr Asp
305             310             315             320

Lys Glu Met Glu Val Leu His Leu Arg Asn Val Ser Phe Glu Asp Ala
            325             330             335

Gly Glu Tyr Thr Cys Leu Ala Gly Asn Ser Ile Gly Leu Ser His His
            340             345             350

Ser Ala Trp Leu Thr Val Leu Glu Ala Leu Glu Glu Arg Pro Ala Val
            355             360             365

Met Thr Ser Pro Leu Tyr Leu Glu Ile Ile Ile Tyr Cys Thr Gly Ala
    370             375             380

Phe Leu Ile Ser Cys Met Val Gly Ser Val Ile Val Tyr Lys Met Lys
385             390             395             400

Ser Gly Thr Lys Lys Ser Asp Phe His Ser Gln Met Ala Val His Lys
            405             410             415

Leu Ala Lys Ser Ile Pro Leu Arg Arg Gln Val Thr Val Ser Ala Asp
            420             425             430

Ser Ser Ala Ser Met Asn Ser Gly Val Leu Leu Val Arg Pro Ser Arg
            435             440             445

Leu Ser Ser Ser Gly Thr Pro Met Leu Ala Gly Val Ser Glu Tyr Glu
            450             455             460

Leu Pro Glu Asp Pro Arg Trp Glu Leu Pro Arg Asp Arg Leu Val Leu
465             470             475             480

Gly Lys Pro Leu Gly Glu Gly Cys Phe Gly Gln Val Val Leu Ala Glu
            485             490             495

Ala Ile Gly Leu Asp Lys Asp Lys Pro Asn Arg Val Thr Lys Val Ala
            500             505             510

Val Lys Met Leu Lys Ser Asp Ala Thr Glu Lys Asp Leu Ser Asp Leu
    515             520             525

Ile Ser Glu Met Glu Met Met Lys Met Ile Gly Lys His Lys Asn Ile
    530             535             540

Ile Asn Leu Leu Gly Ala Cys Thr Gln Asp Gly Pro Leu Tyr Val Ile
545             550             555             560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
            770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 2
<211> LENGTH: 5917
<212> TYPE: DNA
<213> ORGANISM: Homo sapiens
<300> PUBLICATION INFORMATION:
<308> DATABASE ACCESSION NUMBER: NM_023110
<309> DATABASE ENTRY DATE: 2007-03-01
<313> RELEVANT RESIDUES IN SEQ ID NO: (1)..(5917)

<400> SEQUENCE: 2
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc aggggcgga ggcggaggag ggaccagcgc gggtgggagt gagagagcga     180
gccctcgcgc cccgccggcg catagcgctc ggagcgctct tgcggccaca ggcgcggcgt     240
cctcggcggc gggcggcagc tagcgggagc cgggacgccg gtgcagccgc agcgcgcgga     300
ggaacccggg tgtgccggga gctgggcggc acgtccgga cgggaccgag acccctcgta     360
gcgcattgcg gcgacctcgc cttccccggc cgcgagcgcg ccgctgcttg aaaagccgcg     420
gaacccaagt acttttctcc ggtccgagct cggggcgccc cgcagggcgc acggtacccg     480
tgctgcagtc gggcacgccg cggcgccggg gcctccgcag ggcgatggag cccggtctgc     540

-continued

```
aaggaaagtg aggcgccgcc gctgcgttct ggaggagggg ggcacaaggt ctggagaccc      600
cgggtggcgg acgggagccc tccccccgcc ccgcctccgg ggcaccagct ccggctccat      660
tgttcccgcc cgggctggag gcgccgagca ccgagcgccg ccgggagtcg agcgccggcc      720
gcggagctct tgcgacccg ccaggacccg aacagagccc gggggcggcg ggccggagcc       780
ggggacgcgg gcacacgccc gctcgcacaa gccacggcgg actctcccga ggcggaacct      840
ccacgccgag cgagggtcag tttgaaaagg aggatcgagc tcactgtgga gtatccatgg      900
agatgtggag ccttgtcacc aacctctaac tgcagaactg ggatgtggag ctggaagtgc      960
ctcctcttct gggctgtgct ggtcacagcc acactctgca ccgctaggcc gtccccgacc     1020
ttgcctgaac aagcccagcc ctggggagcc cctgtggaag tggagtcctt cctggtccac     1080
cccggtgacc tgctgcagct tcgctgtcgg ctgcgggacg atgtgcagag catcaactgg     1140
ctgcgggacg gggtgcagct ggcggaaagc aaccgcaccc gcatcacagg ggaggaggtg     1200
gaggtgcagg actccgtgcc cgcagactcc ggcctctatg cttgcgtaac cagcagcccc     1260
tcgggcagtg acaccaccta cttctccgtc aatgtttcag atgctctccc ctcctcggag     1320
gatgatgatg atgatgatga ctcctcttca gaggagaaag aaacagataa caccaaacca     1380
aaccgtatgc ccgtagctcc atattggaca tccccagaaa agatggaaaa gaaattgcat     1440
gcagtgccgg ctgccaagac agtgaagttc aaatgccctt ccagtgggac ccaaaacccc     1500
acactgcgct ggttgaaaaa tggcaaagaa ttcaaacctg accacagaat tggaggctac     1560
aaggtccgtt atgccacctg gagcatcata atggactctg tggtgccctc tgacaagggc     1620
aactacacct gcattgtgga gaatgagtac ggcagcatca accacacata ccagctggat     1680
gtcgtggagc ggtcccctca ccggcccatc ctgcaagcag ggttgcccgc caacaaaaca     1740
gtggccctgg gtagcaacgt ggagttcatg tgtaaggtgt acagtgaccc gcagccgcac     1800
atccagtggc taaagcacat cgaggtgaat gggagcaaga ttggcccaga caacctgcct     1860
tatgtccaga tcttgaagac tgctggagtt aataccaccg acaaagagat ggaggtgctt     1920
cacttaagaa atgtctcctt tgaggacgca ggggagtata cgtgcttggc gggtaactct     1980
atcggactct cccatcactc tgcatggttg accgttctgg aagccctgga agagaggccg     2040
gcagtgatga cctcgcccct gtacctggag atcatcatct attgcacagg ggccttcctc     2100
atctcctgca tggtggggtc ggtcatcgtc tacaagatga gagtggtac caagaagagt     2160
gacttccaca gccagatggc tgtgcacaag ctggccaaga gcatccctct gcgcagacag     2220
gtaacagtgt ctgctgactc cagtgcatcc atgaactctg ggttcttct ggttcggcca      2280
tcacggctct cctccagtgg gactcccatg ctagcagggg tctctgagta tgagcttccc     2340
gaagaccctc gctgggagct gcctcgggac agactggtct taggcaaacc cctgggagag     2400
ggctgctttg gcaggtggt gttggcagag gctatcgggc tggacaagga caaacccaac      2460
cgtgtgacca agtggctgt gaagatgttg aagtcggacg caacagagaa agacttgtca      2520
gacctgatct cagaaatgga gatgatgaag atgatcggga agcataagaa tatcatcaac      2580
ctgctggggg cctgcacgca ggatggtccc ttgtatgtca tcgtggagta tgcctccaag      2640
ggcaacctgc gggagtacct gcaggccgg aggcccccag ggctggaata ctgctacaac       2700
cccagccaca cccagagga gcagctctcc tccaaggacc tggtgtcctg cgcctaccag       2760
gtggcccgag gcatggagta tctggcctcc aagaagtgca tacaccgaga cctggcagcc     2820
aggaatgtcc tggtgacaga ggacaatgtg atgaagatag cagactttgg cctcgcacgg     2880
gacattcacc acatcgacta ctataaaaag acaaccaacg gccgactgcc tgtgaagtgg     2940
```

```
atggcacccg aggcattatt tgaccggatc tacacccacc agagtgatgt gtggtctttc   3000
ggggtgctcc tgtgggagat cttcactctg ggcggctccc catacccgg  tgtgcctgtg   3060
gaggaacttt tcaagctgct gaaggagggt caccgcatgg acaagcccag taactgcacc   3120
aacgagctgt acatgatgat gcgggactgc tggcatgcag tgccctcaca gagacccacc   3180
ttcaagcagc tggtggaaga cctggaccgc atcgtggcct tgacctccaa ccaggagtac   3240
ctggacctgt ccatgcccct ggaccagtac tcccccagct ttcccgacac ccggagctct   3300
acgtgctcct caggggagga ttccgtcttc tctcatgagc cgctgcccga ggagccctgc   3360
ctgccccgac acccagccca gcttgccaat ggcggactca aacgccgctg actgccaccc   3420
acacgccctc cccagactcc accgtcagct gtaaccctca cccacagccc ctgctgggcc   3480
caccacctgt ccgtccctgt ccccttccct gctggcagga gccggctgcc taccaggggc   3540
cttcctgtgt ggcctgcctt cacccactc  agctcacctc tccctccacc tcctctccac   3600
ctgctggtga gaggtgcaaa gaggcagatc tttgctgcca gccacttcat cccctcccag   3660
atgttggacc aacacccctc cctgccacca ggcactgcct ggagggcagg gagtgggagc   3720
caatgaacag gcatgcaagt gagagcttcc tgagctttct cctgtcggtt tggtctgttt   3780
tgccttcacc cataagcccc tcgcactctg gtggcaggtg ccttgtcctc agggctacag   3840
cagtagggag gtcagtgctt cgtgcctcga ttgaaggtga cctctgcccc agataggtgg   3900
tgccagtggc ttattaattc cgatactagt ttgctttgct gaccaaatgc ctggtaccag   3960
aggatggtga ggcgaaggcc aggttggggg cagtgttgtg gccctgggc  ccagccccaa   4020
actgggggct ctgtatatag ctatgaagaa aacacaaagt gtataaatct gagtatatat   4080
ttacatgtct ttttaaaagg gtcgttacca gagatttacc catcgggtaa gatgctcctg   4140
gtggctggga ggcatcagtt gctatatatt aaaaacaaaa aagaaaaaaa aggaaaatgt   4200
ttttaaaaag gtcatatatt ttttgctact tttgctgttt tattttttta aattatgttc   4260
taaacctatt ttcagtttag gtccctcaat aaaaattgct gctgcttcat ttatctatgg   4320
gctgtatgaa aagggtggga atgtccactg gaaagaaggg acacccacgg gccctggggc   4380
taggtctgtc ccgagggcac cgcatgctcc cggcgcaggt tccttgtaac ctcttcttcc   4440
taggtcctgc acccagacct cacgacgcac ctcctgcctc tccgctgctt ttggaaagtc   4500
agaaaaagaa gatgtctgct tcgagggcag gaacccatc  catgcagtag aggcgctggg   4560
cagagagtca aggcccagca gccatcgacc atggatggtt tcctccaagg aaaccggtgg   4620
ggttgggctg gggaggggggc acctacctag gaatagccac gggggtagagc tacagtgatt   4680
aagaggaaag caagggcgcg gttgctcacg cctgtaatcc cagcactttg ggacaccgag   4740
gtgggcagat cacttcaggt caggagtttg agaccagcct ggccaactta gtgaaacccc   4800
atctctacta aaaatgcaaa aattatccag gcatggtggc acacgcctgt aatcccagct   4860
ccacaggagg ctgaggcaga atcccttgaa gctgggaggc ggaggttgca gtgagccgag   4920
attgcgccat tgcactccag cctgggcaac agagaaaaca aaaggaaaa  caaatgatga   4980
aggtctgcag aaactgaaac ccagacatgt gtctgccccc tctatgtggg catggttttg   5040
ccagtgcttc taagtgcagg agaacatgtc acctgaggct agttttgcat tcaggtccct   5100
ggcttcgttt cttgttggta tgcctcccca gatcgtcctt cctgtatcca tgtgaccaga   5160
ctgtatttgt tgggactgtc gcagatcttg gcttcttaca gttcttcctg tccaaactcc   5220
atcctgtccc tcaggaacgg ggggaaaatt ctccgaatgt ttttggtttt ttggctgctt   5280
ggaatttact tctgccacct gctggtcatc actgtcctca ctaagtggat tctggctccc   5340
```

```
ccgtacctca tggctcaaac taccactcct cagtcgctat attaaagctt atattttgct    5400
ggattactgc taaatacaaa agaaagttca atatgttttc atttctgtag ggaaaatggg    5460
attgctgctt taaatttctg agctagggat tttttggcag ctgcagtgtt ggcgactatt    5520
gtaaaattct ctttgtttct ctctgtaaat agcacctgct aacattacaa tttgtattta    5580
tgtttaaaga aggcatcatt tggtgaacag aactaggaaa tgaattttta gctcttaaaa    5640
gcatttgctt tgagaccgca caggagtgtc tttccttgta aaacagtgat gataatttct    5700
gccttggccc taccttgaag caatgttgtg tgaagggatg aagaatctaa aagtcttcat    5760
aagtccttgg gagaggtgct agaaaaatat aaggcactat cataattaca gtgatgtcct    5820
tgctgttact actcaaatca cccacaaatt tccccaaaga ctgcgctagc tgtcaaataa    5880
aagacagtga aattgacctg aaaaaaaaaa aaaaaa                             5917

<210> SEQ ID NO 3
<211> LENGTH: 30
<212> TYPE: DNA
<213> ORGANISM: Artificial
<220> FEATURE:
<223> OTHER INFORMATION: primer No.5'-3

<400> SEQUENCE: 3
acgggatcca ggaccctggc tggagagaca                                       30

<210> SEQ ID NO 4
<211> LENGTH: 29
<212> TYPE: DNA
<213> ORGANISM: Artificial
<220> FEATURE:
<223> OTHER INFORMATION: primer No.3'-5

<400> SEQUENCE: 4
aagctcgagc cgccggaacc gcggccgga                                        29
```